United States Patent
Hum et al.

(10) Patent No.: US 11,485,891 B2
(45) Date of Patent: Nov. 1, 2022

(54) PRODUCTS AND METHODS FOR THE TREATMENT OF MIXTURES OF WATER AND HYDROPHOBIC LIQUIDS

(71) Applicant: B.C. RESEARCH INC., Vancouver (CA)

(72) Inventors: Gabriel Hum, Langley (CA); Daniel Zachary Kurek, Vancouver (CA); Anwu Li, Richmond (CA)

(73) Assignee: B.C. RESEARCH INC., Vancouver (CA)

( * ) Notice: Subject to any disclaimer, the term of this patent is extended or adjusted under 35 U.S.C. 154(b) by 34 days.

(21) Appl. No.: 17/250,130

(22) PCT Filed: Jun. 5, 2019

(86) PCT No.: PCT/CA2019/050785
§ 371 (c)(1),
(2) Date: Dec. 3, 2020

(87) PCT Pub. No.: WO2019/232629
PCT Pub. Date: Dec. 12, 2019

(65) Prior Publication Data
US 2021/0230466 A1  Jul. 29, 2021

Related U.S. Application Data

(60) Provisional application No. 62/680,950, filed on Jun. 5, 2018.

(51) Int. Cl.
*C09K 3/32* (2006.01)
*C02F 1/68* (2006.01)
(Continued)

(52) U.S. Cl.
CPC ............ *C09K 3/32* (2013.01); *C02F 1/68* (2013.01); *C07C 237/22* (2013.01); *C02F 2101/32* (2013.01); *C02F 2103/08* (2013.01)

(58) Field of Classification Search
USPC ........ 210/691; 252/60; 507/90, 935; 516/98, 516/902
See application file for complete search history.

(56) References Cited

U.S. PATENT DOCUMENTS 3,810,835 A * 5/1974 Ferm ................ C02F 1/682
516/74
3,969,087 A * 7/1976 Saito ................ A61K 8/44
516/102
(Continued)

FOREIGN PATENT DOCUMENTS

JP  4614357  4/1971
JP  4966726  6/1974
(Continued)

OTHER PUBLICATIONS

Chernyavskaya et al., "Synthesis and antibacterial activity of iodides of N-acylglycyl- and N-acylalanylhydrazones of N-alkylpyridinium-4-aldehyde", Khimiko Farmatsevticheskii Zhurnal, vol. 21(8), pp. 968-971, 1987.

(Continued)

*Primary Examiner* — Nina Bhat
(74) *Attorney, Agent, or Firm* — McKee, Voorhees & Sease, PLLC

(57) ABSTRACT

The invention relates to chemical-based methods and products for mitigating the impact of an oil spill, that act via mechanisms which include reducing adhesiveness, herding, thickening and gelling. N-fatty acid amino acid (FA-AA) conjugates display oil-herding behavior when formulated as a salt, or the free acid in water-miscible organic solvents. Various salts of FA-AA conjugates are water soluble and can herd oils and increase the thickness of the oil layer. Replacement of the acid group of fatty acid α-amino acid conjugates
(Continued)

with other groups that act as hydrogen bond donors and acceptors results in potent phase selective organo gellants. The oil thickeners or gellants include can be prepared from biobased feedstocks, have low toxicity, high capacity for oil and reduction of the need to use an organic solvent to apply the thickener or gellant to an oil and water mixture in order to gel the oil phase.

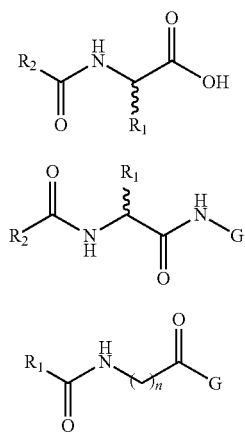

26 Claims, 5 Drawing Sheets

(51) Int. Cl.
  *C07C 237/22* (2006.01)
  *C02F 101/32* (2006.01)
  *C02F 103/08* (2006.01)

(56) References Cited

U.S. PATENT DOCUMENTS

| | | | | |
|---|---|---|---|---|
| 4,462,910 A | * | 7/1984 | Lepain | C02F 3/344 516/67 |
| 4,512,914 A | * | 4/1985 | Lepain | C02F 1/682 516/74 |
| 4,686,053 A | * | 8/1987 | Baviere | C09K 8/584 507/938 |
| 4,830,759 A | * | 5/1989 | Charlier | C09K 3/32 516/74 |
| 5,131,921 A | * | 7/1992 | Sung | C10L 10/04 44/389 |
| 5,238,575 A | * | 8/1993 | Waldmann | C02F 1/681 210/691 |
| 5,459,066 A | * | 10/1995 | Mestetsky | B01D 17/00 210/708 |
| 5,514,588 A | * | 5/1996 | Varadaraj | B09C 1/10 424/76.8 |
| 8,697,614 B2 | * | 4/2014 | Choban | C10G 1/04 507/242 |
| 2006/0062751 A1 | * | 3/2006 | Sato | A61K 8/44 548/537 |
| 2006/0073177 A1 | * | 4/2006 | Yamato | A61Q 19/00 424/401 |
| 2012/0201863 A1 | | 8/2012 | John et al. | |
| 2013/0095562 A1 | * | 4/2013 | Perry | C10G 1/047 507/201 |
| 2014/0141978 A1 | * | 5/2014 | Narayanan | A01N 25/04 504/206 |

FOREIGN PATENT DOCUMENTS

| | | |
|---|---|---|
| WO | 9014429 A1 | 11/1990 |
| WO | 2012071293 A2 | 5/2012 |
| WO | 2016094682 A2 | 6/2016 |
| WO | 2017026944 A1 | 2/2017 |

OTHER PUBLICATIONS

International Searching Authority in connection with PCT/CA2019/050785 filed Jun. 5, 2019, "International Search Report", 6 pages, dated Aug. 9, 2019.
Motulsky et al., "Characterization and biocompatibility of organogels based on 1-alanine for parenteral drug delivery implants", Biomaterials, vol. 26, pp. 6242-6253, https://www.sciencedirect.com/science/article/pii/S0142961205002905, May 23, 2005.
Radley et al., "Potassium Salts of Acylated Amino Acids as Chiral Dopants and Hosts in the Formation of Amphiphilic Cholesteric Liquid Crystals", Mol. Cryst. Liq. Cryst., vol. 231, pp. 183-190, 1993.
Ueda et al., "Syntheses and antimicrobial activity of 2-acylaminothiazole-carboxylic acid and its related compounds", Yakugalcu Zasshi, vol. 79(7), pp. 925-930, Jul. 25, 1959.
Weinbach et al., "Effect of cosolvent on the lateral order of spontaneously formed amphiphilic amide two-dimensional crystallites at the air-solution interface", Journal of the American Chemical Society, vol. 115, No. 24, pp. 11110-11118, Dec. 1, 1993.
Weinbach et al., "Control of Structure and Growth of Polymorphic Crystalline Thin Films of Amphiphilic Molecules on Liquid Surfaces", Science, vol. 264 (5165), pp. 1566-1570, Jun. 10, 1994.

* cited by examiner

PRODUCTS AND METHODS FOR THE TREATMENT OF MIXTURES OF WATER AND HYDROPHOBIC LIQUIDS

CROSS REFERENCE TO RELATED APPLICATIONS

This is a U.S. national phase application claiming priority to PCT/CA2019/050785, filed Jun. 5, 2019, which claims priority under 35 U.S.C. § 119 to provisional application U.S. Ser. No. 62/680,950, filed Jun. 5, 2018, the entire contents of which are hereby incorporated by reference in their entirety.

FIELD OF THE INVENTION

This invention pertains to chemical-based methods and products for treating mixtures of water and hydrophobic liquids with particular utility in the field of oil spill response. Specifically, the invention relates to methods and agents utilized to mitigate the impact of a spill and facilitate oil recovery. The agents act via a range of mechanisms which include reducing adhesiveness, herding, thickening (increased viscosity) and gelling.

BACKGROUND

Methods for treating mixtures of water and hydrophobic liquids facilitate the separation of the two phases and allow for removal and recovery of the hydrophobic liquid phase. An example of scenarios that would benefit from improved methods of separating water and hydrophobic liquids are marine oil spills where oil products are accidently discharged into the environment and come into contact with bodies of water. Spills may result from a variety of operations, including the production and transportation of oil products. Historically, two spill incidents of note are the 1989 grounding of the tanker Exxon Valdez in Alaska and the 2010 BP Horizon drilling rig blowout in the Gulf of Mexico, which resulted in an estimated 260 K and 4.9 M barrels of oil released, respectively. Oil spills cause significant environmental damage and also have potentially severe social and economic impacts. The damage caused by oil spills has spurred on the development of new oil spill treating methods and agents. Some of these materials and methods have been commercialized but there is need for improvement and further development.

Oil spills are time-sensitive events in which faster response times increase the chances of better outcomes, as measured by the extent of oil recovered or removed and the lessened environmental impact. Oil spills evolve rapidly over time. The oil itself spreads and undergoes weathering processes which compounds the difficulty of recovery and removal. Immobilization of the oil or its conversion to a cohesive mass to prevent or hinder its spread and reduce the surface area for weathering is a viable strategy to limit the impact of a spill and improve the recovery of the spilled oil. Maximal advantages would be gained if the spill could be treated promptly, i.e., within a rapid response time window prior to the arrival of the larger oil spill response contingency.

Depending upon the nature of the oil, adhesion to plant and animal life, structures and substrates can be an additional negative behaviour of an oil slick. Remediation typically entails removal of the oil using washing agents or washing procedures resulting in dispersed oil which is either released into the environment or collected for disposal. An alternative remediation strategy is to remove the contaminated materials for disposal.

To minimize these negative impacts, different spill treating agents (STA) have been proposed or developed such as herders, sorbents, solidifiers and gellants.

Herding agents or oil-herders are a class of STAs which are employed to increase the thickness of oil slicks by reducing their surface area. They typically act by modifying the balance of surface and interfacial tension of the oil and water phases. The reduction in surface area and increase in slick thickness can be used as a precursor treatment to subsequent oil recovery or removal methods which may include skimming, the use of solidifiers and/or sorbents and in situ burning.

Oil-herders or herding agents are described in the prior art, including:
- U.S. Pat. No. 3,810,835 (Ferm)
- U.S. Pat. No. 3,959,134 (Canevari)
- U.S. Pat. No. 9,797,109 (Takamura et al.)
- Rodriguez, J. L.; Ciolino, A. E.; Pieroni, O. I.; Vuano, B. M.; Schulz, P. C.; *Journal of Surface Science and Technology* 23 (3-4), p. 111 (2007).
- "Research on Using Oil Herding Agents for Rapid Response In Situ Burning of Oil Slicks on Open Water" by S.L. Ross Environmental Research Ltd. for U.S. Department of the Interior Bureau of Safety and Environmental Enforcement Oil Spill Response Research (OSRR) Program (2012)
- "Recent Efforts to Develop and Commercialize Oil Herders" Lane, P.; Newsom, P.; Buist, I.; Nedwed, T.; Tidwell, A.; Flagg, K.; Proceedings of the 37$^{th}$ Arctic Marine Oilspill Program Technical Seminar on Environmental Contamination and Response (2012)
- Gupta, D.; Sarker, B.; Thadikaran, K.; John, V.; Maldarelli, C.; John, G.; *Sci. Adv.* 1(5), p. 1, (2015)

Oil-herders or herding agents reported in the literature incorporate a diverse range of chemistries. One commercially available herder is based upon silicon polymer chemistry. Though effective at low dosages, the biological properties of these polymers are not well understood. Silicon polymers are generally very stable and thus unlikely to readily undergo biodegradation and thus likely to bioaccumulate. The long-term environmental effects of silicon-based polymers are not well understood. More recently, non-ionic surfactants based upon polyethylene glycol polymers have been proposed as oil-herders. These man-made polymers are also generally resistant to biodegradation and similarly understudied in terms of long-term environmental effects.

Slick 6535 (trademark) is a commercially available oil-herder which has been under development over the course of at least two decades. The key component is SPAN-20 (trademark) or sorbitan monolaurate. This ester suffers from poor solubility and is formulated with an organic solvent to facilitate its application. The organic solvent is listed as a potential irritant, but in general, its environmental toxicity is not well understood.

To date, the most common proposed use of oil-herders is application to increase the thickness of oil slicks as a pre-treatment stage to promote in situ burning and skimming operations. They are effective at low dosages but the poorly understood environmental fates of silicon-based and polyethylene glycol based herders do represent liabilities.

Among the best currently available spill treating agents for the binding of spilled oils are a class of reagents referred to as solidifiers and sorbents. These materials typically interact with the oil via absorption and adsorption processes to convert the oil into a solid cohesive mass which is composed of the sorbent or solidifier and the oil. The compositions of sorbents and solidifiers may vary greatly and range from synthetic polymers to those based on natural materials (e.g., cellulose, sawdust). The concept and use of sorbents as STAs dates back over 50 years. They are typically applied in small spill situations and are not generally regarded as a viable option in large spills. A limiting factor in their widespread application is their capacity for oil. Commercial sorbents typically have loading requirement of 20-40% w/v. For each liter of oil spilled, 200-400 g of sorbent material is required, requiring large quantities of sorbent to be available and handled and resulting in the generation of a large waste stream which requires special disposal considerations.

Gellants are substances which are used to produce a gel. There may be inherent advantages in using gellants to render spilled oil into a gel state in order to prevent or hinder the spreading and weathering processes. This strategy has been proposed by a variety of groups. The use of small molecule based gellants (SMGs) offers potential advantages. Gellants based upon small molecules (MW<3000) exert gel formation by self-assembling into supramolecular structures such as fibers. The structures form a three-dimensional network which traps the solvent (i.e. the oil) and the result is a cohesive mass which ranges in viscosity from a thickened liquid to a gel state. A subclass of SMGs are gellants capable of selectively gelling a single phase. In an oil spill scenario, selective gelling of the oil phase would present obvious advantages. Phase selective organo gellants (PSOGs) are agents which induce gel formation of a hydrophobic liquid phase in the presence of a second non-miscible phase which is typically water. When introduced into an oil-water liquid mixture, the PSOGs partition into the organic phase and induce gel formation. The presence of the water does not hinder the gel formation process.

Existing PSOGs suffer from certain features which have thus far prevented their adoption as an STA. Most PSOGs reported are amphiphilic molecules which have both hydrophilic and lipophilic properties and have low solubility in both aqueous and hydrophobic phases at ambient temperature. As a result, there are two common routes to gel formation using PSOGs. In the first approach, the PSOG is solubilized in a compatible organic carrier solvent. This solution is then applied to a hydrophobic liquid (i.e., oil) and water mixture. The second approach involves adding the PSOG as a solid to an oil-water mixture followed by the application of heat to solubilize the PSOG in the oil phase. Gel formation occurs upon cooling of the oil to ambient temperature. Neither of these typical routes of applying PSOGs is viable in a real-world oil spill scenario since heating an oil spill in situ would not be practical while use of an organic carrier solvent requires large volumes of solvent to be handled and adds significant safety (due to flammability) and environmental toxicity concerns.

Most PSOGs reported in the literature are comprised of complex molecules which have at least one stereo center and reportedly require enantiopure material for gel action to occur. In many instances, the molecules have multiple chiral centers. The inclusion of chiral centers and need for enantiopure materials typically represent disincentives due to increased complexity of synthesis and increased costs of starting materials. For PSOGs to serve as a viable STA option, there is a need for improvement in multiple aspects of these molecules, namely, design, application, performance and preparation.

The use of phase selective organo gellants as a means oil spill remediation has been described in the prior art, including:

US 2012/0201863 A1 (John et al.)
WO 2017/026944 (Zeng et al.)
Bhattacharya, S.; Krishnan-Ghosh, Y.; *Chemical Communications* p. 185 (2001)
Vibhute, A. M.; Muvvala, V.; Sureshan, K. M.; *Angew. Chem. Int. Ed.* 55, p. 7782, (2016)
Samateh, M.; Vidyasagar, A.; Jadhav, S. R.; John, G.; RSC Adv. 6, p. 107598, (2016)
Ren, C.; Shen, J.; Chen, F.; Zeng, H.; *Angew. Chem. Int. Ed.* 56, p. 3847, (2017)
Jadhav, S.; Vemula, P. K.; Kumar, R.; Srinivasza, R.; John, G.; *Angew. Chem. Int. Ed.* 49, p. 7695, (2010)
Organo gellants are described in the prior art in:
Pal, A.; Dey, J.; *Langmuir* 27, p. 3401, (2011)
Pal.; Mahapatra, R. D.; Dey, J.; *Langmuir* 30, p. 13791, (2014)
Pal, A.; Patra, T.; Dey, J.; *Chemical Physics Letter* 556, p. 245, (2013)

There are currently no commercially-available oil thickeners (i.e. oil viscosity enhancers) or gellants based upon small molecule phase selective organo gellants for use as oil spill control agents. There are numerous examples of compounds which have been proposed as potential spill treating agents in both the patent and non-patent literature. The range of molecules which have been reported to selectively gel a hydrophobic organic phase in the presence of water represents diverse structural classes.

As discussed, current PSOGs suffer from limited appeal due to the required method of application. Common practice reported in the prior art is the method of application whereby the PSOG is added as a solid to the oil-water mixture. The entire mixture is then heated to dissolve the gellant and, upon cooling, a gel of the hydrophobic phase forms. This is clearly not practical for a real world oil spill.

Alternatively, the PSOG is dissolved into an organic solvent with heating if necessary. The solution is then applied to an oil-water mixture. Upon mixing, the water-miscible solvent enters the water phase and the PSOG partitions into the organic phase to undergo self-assembly and effect gel formation. This is somewhat more practical than heating the oil spill itself; however, it still requires large quantities of often flammable organic solvent to be stored and delivered on site in the event of a spill. Depending upon the nature of the organic solvent, it may be gelled with the oil or released into the environment.

The use of a high proportion of organic solvent to apply PSOGs onto a spill is associated with safety issues and concerns surrounding environmental toxicity. Since current PSOGs require either an organic solvent or the more impractical in situ heating of an oil spill, the commercialization of PSOGs as STAs still faces significant obstacles.

Bhattacharya et al. (*Chemical Communications* p. 185. 2001) was among the first papers to propose the use of PSOGs as a spill treating agent. It discloses the ability of N-lauroyl-L-alanine, i.e.,

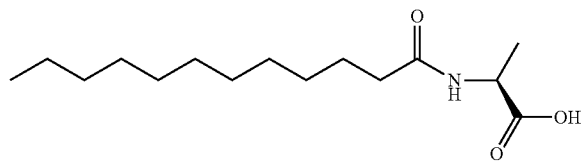 [SMILES: CCCCCCCCCCCC(=O)N[C@@H](C)C(=O)O]

to gel various hydrophobic organic liquids including petrol. The paper is also among the first to report phase selective organo gellants.

More recently, there have been reports of PSOGs which can be added as a solid at room temperature. After incubation at room temperature, gel formation occurs within an hour. Gel formation can be accelerated by using a wetted solid strategy wherein the PSOG is wetted with a water-miscible solvent in which it is has limited solubility. Application of the wetted solid to an oil results in gel formation within half an hour.

Specific examples of PSOGs proposed as oil spill response agents include compounds based upon mannitol disclosed in US 2012/0201863 (John) and organo gelators disclosed in WO 2017/026944 (Zeng) based upon protected amino acids. Examples of such compounds are the following:

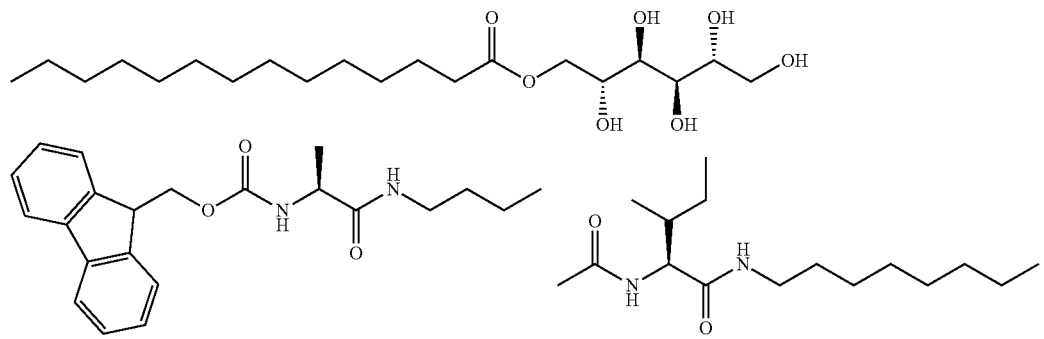

Mannitol-Based and Amino Acid-Based PSOGs

The sugar-based amphiphilic esters disclosed in US 2012/0201863 (John) could affect gel formation when delivered via one of two routes. Typically, the gellant could be added as a solid to a mixture of oil and water which was then heated and agitated to dissolve the solid in the oil phase. Upon standing and cooling, the hydrophobic layer formed a gel. Alternatively, the gellant could be dissolved in a water-miscible solvent, such as ethanol or tetrahydrofuran and added as a solution to an oil-water mixture. As discussed above, neither of these delivery methods are considered viable in an actual oil spill scenario. The former would require heating a large portion of an oil spill while the latter would necessitate the release of large amounts of organic solvent into the environment. Additionally, the sugar-based amphiphilic esters disclosed in US 2012/0201863 are prepared via an enzymatic reaction. This synthesis has a reported 70% yield and requires the vinyl esters of the fatty acids as a feed stock.

Ren et al. (*Angew. Chem. Int. Ed.* 56, p. 3847, 2017) discloses that PSOGs based upon the amino acid isoleucine were capable of gelling various oil products when applied as a powder wetted with acetonitrile (methyl cyanide), which is both toxic and flammable. Gel formation time varied with the nature of the oil and ranged from 9-70 minutes. The loading requirements were also dependent on the type of oil spanning 10-35% w/v.

Pal (see references above) has disclosed achiral organo gellants and demonstrated that amino acids are capable of gelling organic liquids when only a single phase was involved. The work did not demonstrate whether thickening (increased viscosity) or gel formation was possible in the presence of water; however, in either case it was still necessary to heat the hydrophobic phase to dissolve the gellant which formed a gel upon cooling.

To date, no one in the literature has reported an aqueous-only PSOG delivery, nor a dry method which does not require in situ heating to achieve fast gelling kinetics (<5 minutes).

There is a renewed interest in exploring the development and application of oil-herding agents due to their potential versatility. Oil-herders may be used in a variety of strategies, including the protection of structures and environmentally sensitive areas from approaching oil slicks. In addition, oil-herders may be used to prepare a slick for either in situ burning or skimming. Both these operations require a minimum slick thickness in order to be carried out successfully. Current commercially-available oil-herding agents may be improved upon in numerous ways which include: (a) eliminating the use or need for a large proportion of organic carrier solvents; (b) eliminating the use or need of non-biodegradable polymers which have poorly understood environmental effects (i.e., silicon-based and polyethylene-based polymers); and (c) incorporating the use of biodegradable or environmentally benign components.

Oil solidifiers represent a potential strategy towards minimizing the environmental impact of an oil spill via two distinct mechanisms. When applied early during a spill incident, the solidifiers hinder or prevent the spread of the oil. During the recovery and removal phase, solidifiers (i.e., sorbents) may be used when other mechanical means fail (e.g., skimming). There are drawbacks associated with current oil spill clean-up sorbents. The dosing level of sorbents is high, ranging from 20-40% w/v (200-400 g of sorbent per 1 L of oil). Many of the commercial products are composed of polymers which are not biodegradable and may thus act as an environmental hazard if not recovered from the environment. The recovered oil laden spent sorbent is a waste stream which must be disposed of typically via incineration or landfill.

PSOGs represent a subset of oil solidifiers could address some of the shortcomings associated with traditional oil solidifiers of which the majority rely on absorption and adsorption interactions. Based upon what has been reported in the patent and non-patent literature, there is the potential to apply small molecule based phase selective organo gellants as oil spill treating agents. In order to achieve this, certain shortcomings associated with compounds reported in the literature must be addressed which include: (a) the need to use heat to solubilize the gellant in the hydrophobic liquid or the use of an organic delivery solvent to apply the solubilized gellant to the mixture of water and oil; (b) high loading requirements of 10-20% w/v; (c) the need for wetting solvents such as acetonitrile; and (d) long gelling times if dry powders are used without heating.

SUMMARY OF THE INVENTION

Figure 1:
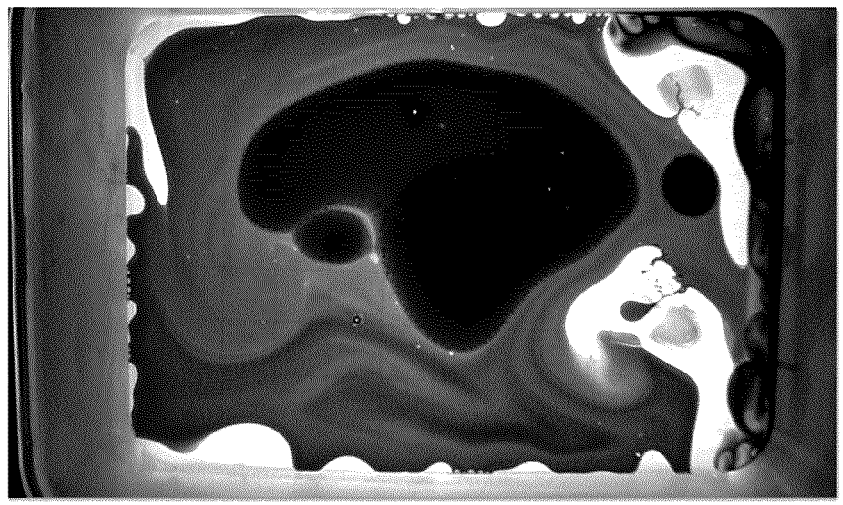
FIG. 1 is a photograph showing oil added to a pan without oil-herder.

According to one embodiment of the invention, there is provided a composition for treating a mixture of oil and water to herd the oil, comprising a compound of Formula I:

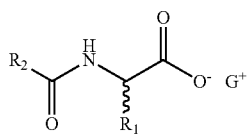
(I)

where:

$R_1$ is selected from the group consisting of:

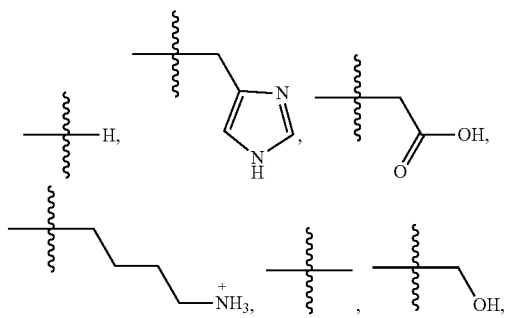

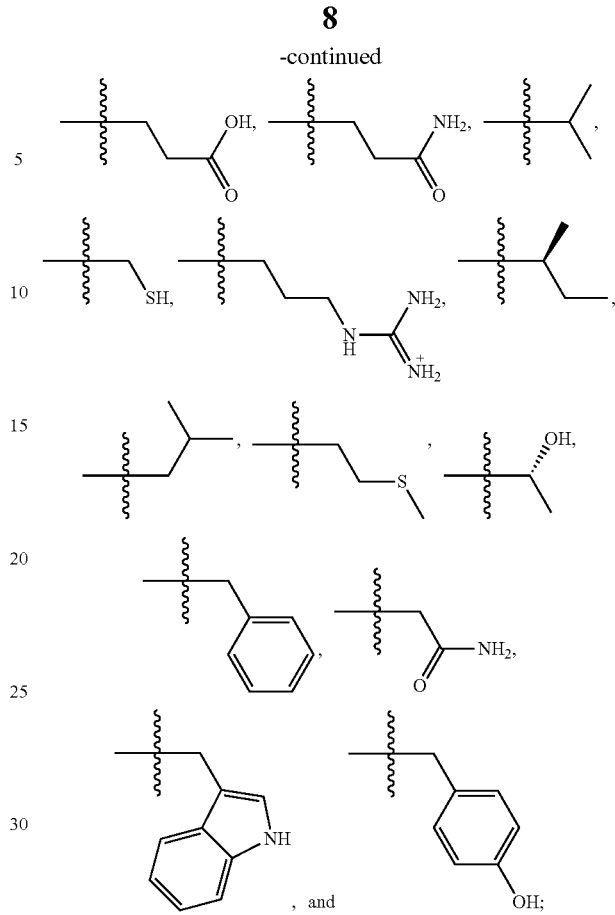

$R_2$ is selected from the group consisting of saturated and unsaturated $C_5$ to $C_{21}$ linear hydrocarbon chains; and G is a cation, for example, Na, K, Li, piperidinium, piperazinium, imidazolium, N-methyl imidazolium, and benzimidazolium.

According to another aspect of the invention, there is provided a composition for treating a mixture of oil and water to herd the oil, comprising a compound of Formula IA:

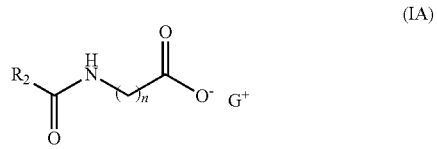
(IA)

where:

$R_2$ is selected from the group consisting of saturated and unsaturated $C_5$ to $C_{21}$ linear hydrocarbon chains;

G is a cation, for example, Na, K, Li, piperidinium, piperazinium, imidazolium, N-methyl imidazolium, and benzimidazolium; and n=1, 2, 3, 4 or 5.

According to another aspect of the invention, there is provided a composition for treating a mixture of oil and water to herd the oil, comprising a water-miscible organic solvent and one or more compounds of Formula IB:

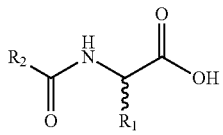
(IB)

where:

$R_1$ is selected from the group consisting of:

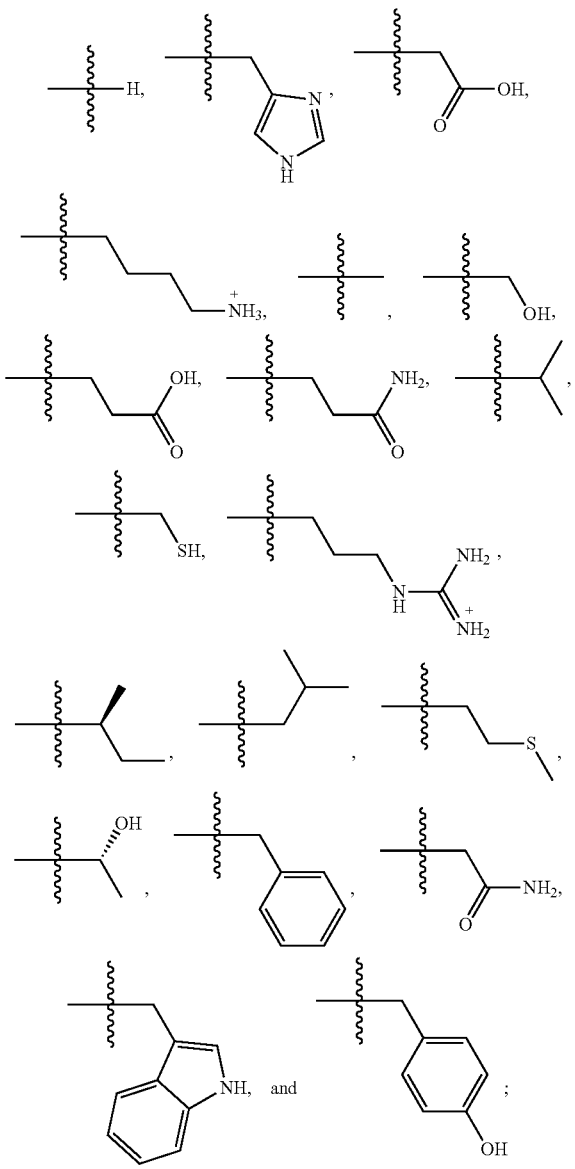

and $R_2$ is selected from the group consisting of saturated and unsaturated $C_5$ to $C_{21}$ linear hydrocarbon chains.

According to another aspect of the invention, there is provided a composition for treating a mixture of oil and water to herd the oil, comprising a water-miscible solvent and one or more compounds of Formula IC:

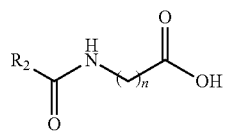
(IC)

where:

$R_2$ is selected from the group consisting of saturated and unsaturated $C_5$ to $C_{21}$ linear hydrocarbon chains; and n=1, 2, 3, 4 or 5.

According to another aspect of the invention, there is provided a composition for treating a mixture of oil and water to gel or increase the viscosity of the oil, comprising a compound of Formula II:

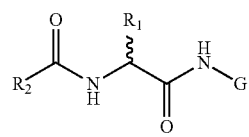
(II)

where:

$R_1$ is selected from the group consisting of:

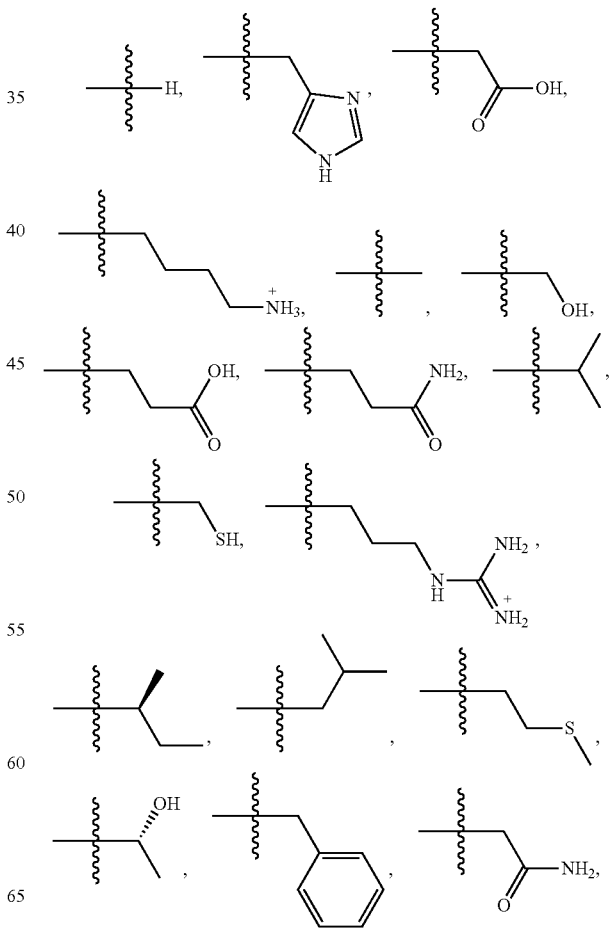

-continued

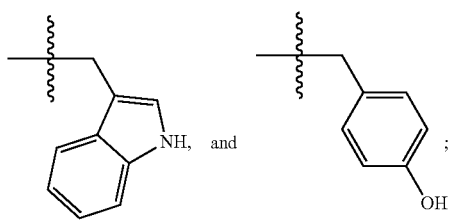

$R_2$ is selected from the group consisting of saturated and unsaturated $C_5$ to $C_{21}$ linear hydrocarbon chains, and

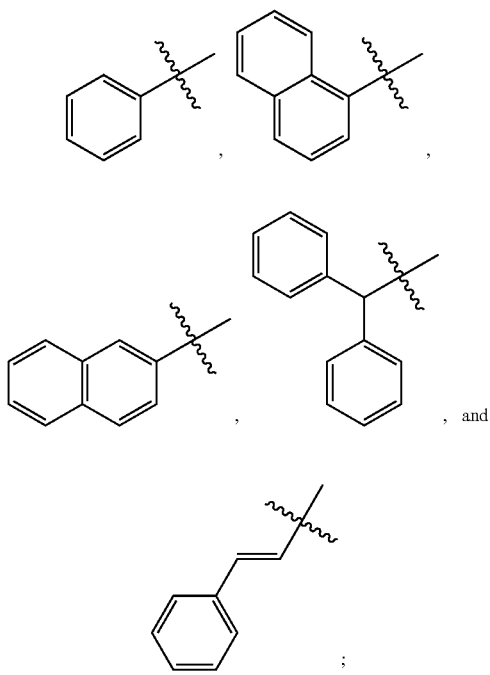

and

G is selected from the group consisting of —H, —CH$_3$, —NH$_2$, —OH, —OCH$_3$, and —(CH$_2$)$_2$OH.

According to a further aspect of the invention, there is provided a composition for treating a mixture of oil and water to thicken or gel the oil, comprising a compound of Formula III:

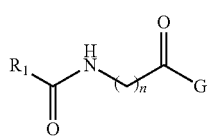

(III)

where:

$R_1$ is selected from the group consisting of saturated and unsaturated $C_5$ to $C_{21}$ linear hydrocarbon chains;

G is selected from the group consisting of —OH, —NH$_2$, —NHNH$_2$, —NOH, NOCH$_3$, and —N(CH$_2$)$_2$OH; and n=2, 3, 4 or 5.

According to a further aspect of the invention, there is provided a compound of Formula IIIA:

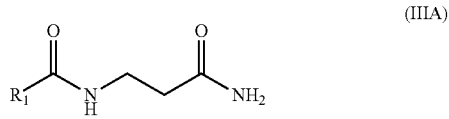

(IIIA)

where $R_1$ is selected from the group consisting of saturated and unsaturated $C_5$ to $C_{21}$ linear hydrocarbon chains.

According to a further aspect of the invention, there is provided a method of treating an oil-water mixture to herd the oil and thereby increase the thickness of the oil layer, the method comprising contacting the oil-water mixture with a composition as aforesaid.

According to a further aspect of the invention, there is provided a method of preventing or minimizing the spread of oil on water and thereby maintaining the thickness of the oil phase, the method comprising pre-treating the water before it is contacted with the oil with a composition as aforesaid.

According to a further aspect of the invention, there is provided a method of reducing the adhesion of oil to solid substrates, the method comprising conditioning the solids with a composition as aforesaid before the solids are contacted with the oil.

According to a further aspect of the invention, there is provided a method of treating an oil-water mixture to gel or increase the viscosity of the oil, comprising suspending one or more compositions or compounds as aforesaid in water to form an aqueous suspension, and adding the aqueous suspension to oil-water mixture.

According to a further aspect of the invention, there is provided a method of treating an oil-water mixture to gel or increase the viscosity of the oil, the method comprising the steps of: (a) preparing a solution or suspension comprising (i) one or more compounds in accordance with Formula II, III or IIIA or compositions as aforesaid and (ii) a carrier solution comprising a water-miscible organic solvent and water, in which the organic solvent comprises in the range 0 to 50% by volume of said carrier solution; and (b) contacting the oil with the solution or suspension prepared in step (a).

According to a further aspect of the invention, there is provided a method of treating an oil and water mixture to gel or increase the viscosity of the oil, the method comprising the steps of: (a) preparing a solution comprising (i) one or more compounds in accordance with Formula II, III or IIIA or compositions as aforesaid and (ii) a water-miscible organic solvent; (b) adding water to the solution prepared in step (a) to precipitate the compound and produce a suspension comprising the precipitated compound, the organic solvent and water, in which the proportion of the organic solvent in the carrier solution is 50% by volume or less; and (c) contacting the oil with the suspension.

According to a further aspect of the invention, there is provided a method of treating an oil-water mixture to gel or increase the viscosity of the oil, the method comprising the steps of: (a) preparing a solution or suspension comprising (i) one or more compounds in accordance with Formula II, III or IIIA or compositions as aforesaid and (ii) a carrier solution comprising a water-miscible organic solvent and water, in which the organic solvent comprises in the range 0 to 50% by volume of said solution, the compound being present in the solution or suspension in the solid state; (b) removing the wetted solids from the suspension; and (c) contacting the oil with the wetted solids.

According to a further aspect of the invention, there is provided a method of treating an oil-water mixture to gel or increase the viscosity of the oil, the method comprising the steps of: (a) preparing a suspension comprising one or more compounds in accordance with Formula II, III or IIIA or composition as aforesaid, wherein the suspension is prepared by (i) adding the compounds or compositions to water, (ii) applying heat to dissolve the solids, and (iii) cooling the solution to precipitate the solids; and (b) contacting the oil with the suspension.

According to a further aspect of the invention, there is provided a method of treating an oil-water mixture comprising the steps of: (a) suspending a supramolecular gellant in water to form a suspension; (b) heating the suspension until the gellant is dissolved; (c) cooling the suspension to form a hydrophobic structure or structures with a high surface area and high void volume; and (d) contacting the hydrophobic structure or structures with an oil-water mixture and thereby gelling the oil.

According to a further aspect of the invention, there is provided a method of treating an oil-water mixture to gel the oil, comprising a composition or a compound according to a preceding aspect of the invention formed as a hydrophobic structure or structures with a high surface area and high void fraction, and adding this "active" suspension to a mixture of the oil in water. These "active" materials will gel hydrophobic liquids such as oils due to the combination of hydrophobicity, high surface area and high void fraction. "Inactive" materials are chemically identical (i.e., no differences in chemical structure), are similarly hydrophobic but lack the high surface area and high void fraction.

According to a further aspect of the invention, there is provided a method of treating an oil-water mixture to gel the oil, the method comprising the steps of: (a) preparing a solution or suspension comprising (i) one or more compounds in accordance with Formula II, III or IIIA as disclosed herein and (ii) a mixture of a water-miscible organic solvent and water, in which the organic solvent comprises in the range of 0 to 50% by volume of said solution; and (b) contacting the oil with the solution or suspension prepared in step (a).

According to a further aspect of the invention, there is provided a method of treating an oil in water to gel the oil, the method comprising the steps of: (a) preparing an active suspension comprising one or more compounds in accordance with Formula II, III or IIIA as disclosed herein where the compound has been heated in water until dissolved and the solution is then cooled to precipitate the compound to form the active suspension; and (b) contacting the oil with the active suspension prepared in step (a).

Benefits and advantages of embodiments of the present invention include, but are not limited to, providing compositions and methods for reducing the area of an oil slick and therefore increasing the thickness of the slick, and compositions and methods to gel or increase the viscosity of the oil. Further benefits of the compositions and compounds disclosed as oil spill herders is that they can be prepared from biobased feedstocks and are biodegradable. Further benefits of the compositions and compounds disclosed as oil thickeners or gellants include preparation from biobased feedstocks, low toxicity, low dosing requirements (i.e., high capacity for oil) and the reduction or elimination of the need to use an organic solvent to apply the thickener or gellant to an oil-water mixture in order to gel the oil phase.

Further aspects of the invention and features of specific embodiments of the invention are described below.

DETAILED DESCRIPTION

This invention provides chemical-based methods and products for treating mixtures of water and hydrophobic liquids with a particular utility in the field of oil spill response. Specifically, the invention provides methods and chemical agents for mitigating the impact of a spill and facilitating oil recovery. The agents act via a range of mechanisms which include herding, reducing adhesiveness, thickening (increased viscosity) and gelling.

Herders

N-fatty acid amino acid (FA-AA) conjugates display oil-herding behavior when formulated as the free acid in water-miscible organic solvents. Appropriate organic solvents include methanol, ethanol and isopropanol. When dissolved in an appropriate solvent and sprayed around the periphery of a layer of oil on water, these oil-herders act to modify the surface tensions of the water and oil and the water-oil interfacial tension and cause the layer of oil to contract. The surface area of the oil layer is reduced and as a result the thickness of the oil layer is increased.

Figure 2:
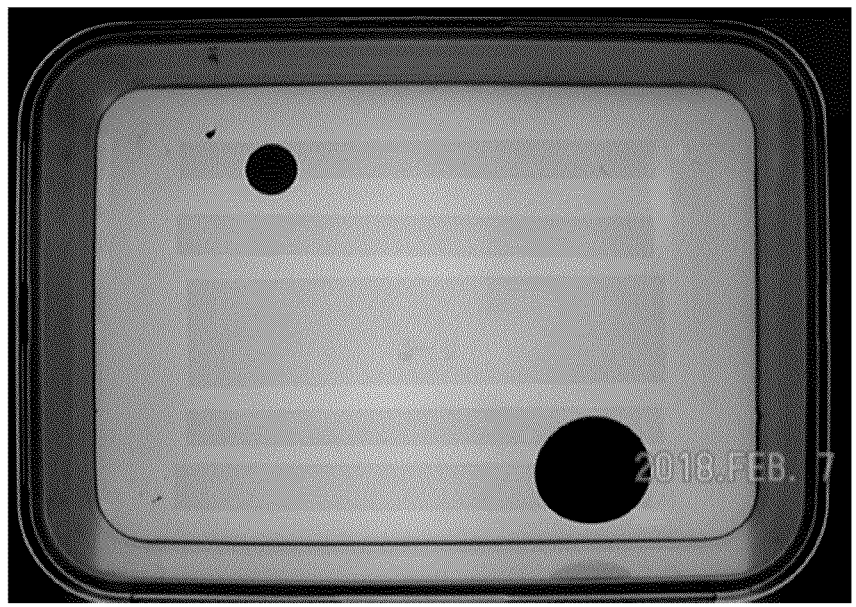
FIG. 2 is a photograph showing oil added to a pan of water pre-dosed with N-fatty acid amino acid salt.

The need for a water-miscible organic solvent can be eliminated if the FA-AA conjugate is formulated as a salt. Various salts of FA-AA conjugates are water soluble and demonstrate the ability to herd oils and increase the thickness of the oil layer. When the FA-AA conjugates in a water-miscible organic solvent or the corresponding salts in water are pre-dosed into water, application of an oil results in contraction of the oil slick where the area of the oil slick is reduced and the thickness of the oil layer is increased. The oil does not spread over the surface. The oil volume and the area of the resulting pooled oil can be used to calculate the thickness of the layer. FIGS. 1 and 2 illustrate the result of oil added to a pan of water without oil-herder, and to a pan of water pre-dosed with an FA-AA salt (sodium tetradecanoylalaninate), respectively. Such a pre-treatment could potentially also be used to protect an environmentally-sensitive area against a spreading oil slick.

When an oil (e.g., dilbit) is applied to water in a pan, the oil spreads to cover the surface of the water. Application of FA-AA as a salt (e.g., Li, Na or K salts) dissolved in water results in contraction of the oil layer. The pooled oil has reduced surface area and greater slick thickness. This is illustrated in FIG. 9A-E where a solution of the salt of a FA-AA is applied to an aliquot of oil which has been allowed to spread in a pan (FIG. 9A). Application of the aqueous herder solution results in contraction of the slick over time. Images taken at 1, 5, 10 and 20 minutes are shown in FIGS. 9B, 9C, 9D and 9E respectively.

Solid substrates (e.g., sand, glass beads) can be pretreated with herder to reduce the adhesion of oil. This can be demonstrated by conditioning the solid substrate (e.g., sand, glass beads) by contacting it with a solution of herder (for example, 0.086 to 10 g/L) for a brief period of time. If oil is then brought into contact with the treated solid substrate for a period of time, the amount of oil that adheres to the substrate can be reduced by 40-50%, depending upon the concentration of herder during the conditioning step.

Formulas I and IA are general formulas of FA-AA compounds which may be formulated as salts in water and have oil-herding properties. The aqueous solutions of these salts can also reduce the amount of oil which adheres to substrates if the substrates are conditioned with the herder solutions before contact with the oil. The stereochemistry is not specified in the instance of the α-amino acids since either enantiomer and racemic mixtures have oil-herding and adhesion reduction properties.

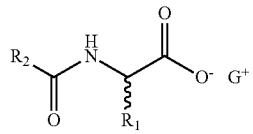

(Formula I)

where:

R₁ is selected from the group consisting of:

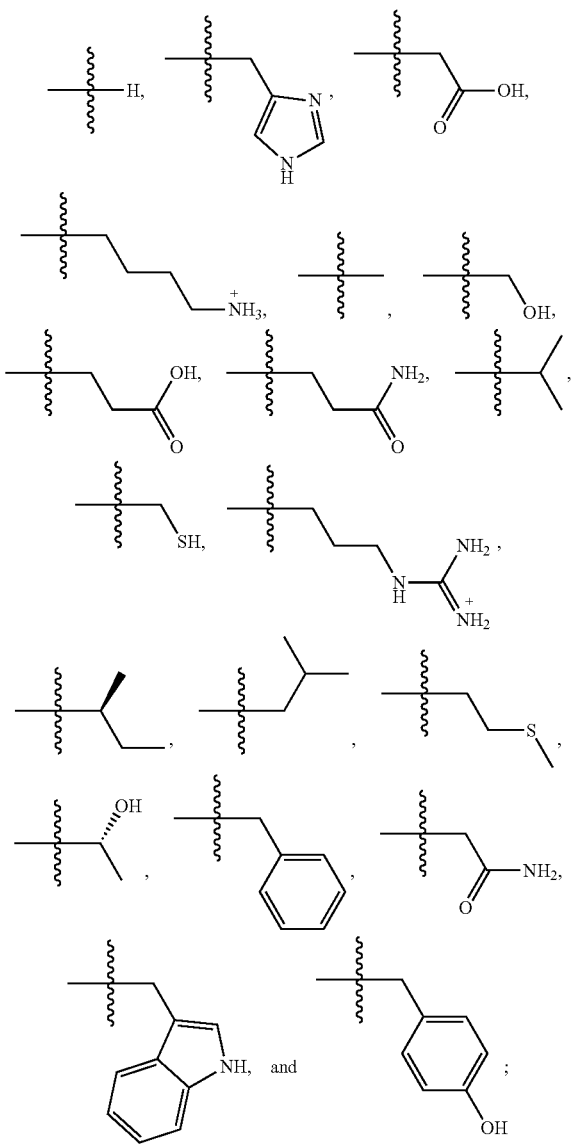

R₂ is selected from the group consisting of saturated and unsaturated $C_5$ to $C_{21}$ linear hydrocarbon chains; and G is a cation such as Na, K, Li, piperidinium, piperazinium, imidazolium, N-methyl imidazolium, and benzimidazolium.

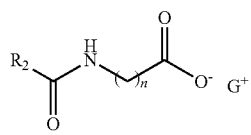

(Formula IA)

where:

R₂ is selected from the group consisting of saturated and unsaturated $C_5$ to $C_{21}$ linear hydrocarbon chains; and G is selected from the group consisting of Na, K, Li, piperidine, piperazine, imidazole, N-methyl imidazole, and benzimidazole; and n=1, 2, 3, 4 or 5.

According to one embodiment, the compound of Formula I comprises L-Alanine, N-(1-oxododecyl)-, sodium salt or its enantiomer or the racemic mixture.

According to another embodiment, the compound of Formula I comprises L-Phenylalanine, N-(1-oxododecyl)-, sodium salt or its enantiomer or the racemic mixture.

According to another embodiment, the compound of Formula I comprises L-Phenylalanine, N-(1-oxotetradecyl)-, sodium salt or its enantiomer or the racemic mixture.

According to another embodiment, the compound of Formula I comprises L-tyrosine, N-(1-oxohexadecyl)-, sodium salt or its enantiomer or the racemic mixture.

Formulas IB and IC are general formulas of the free acids corresponding to the salts of Formulas I and IA. The free acids of Formulas IB and IC may be formulated in water-miscible organic solvents (delivery solvents) to produce solutions which have oil-herding properties. Formulas IB and IC are respectively:

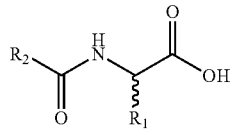

(Formula IB)

where:

R₁ is selected from the group consisting of:

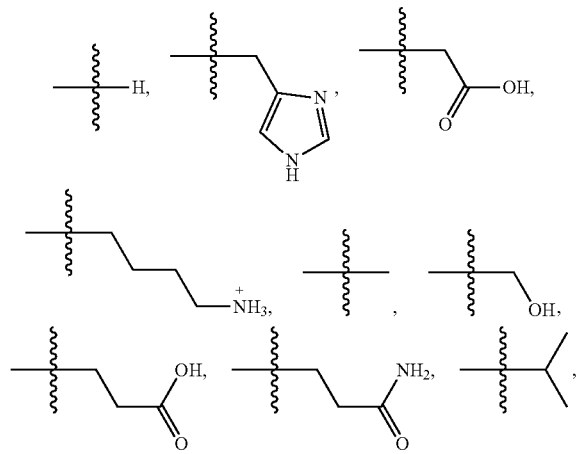

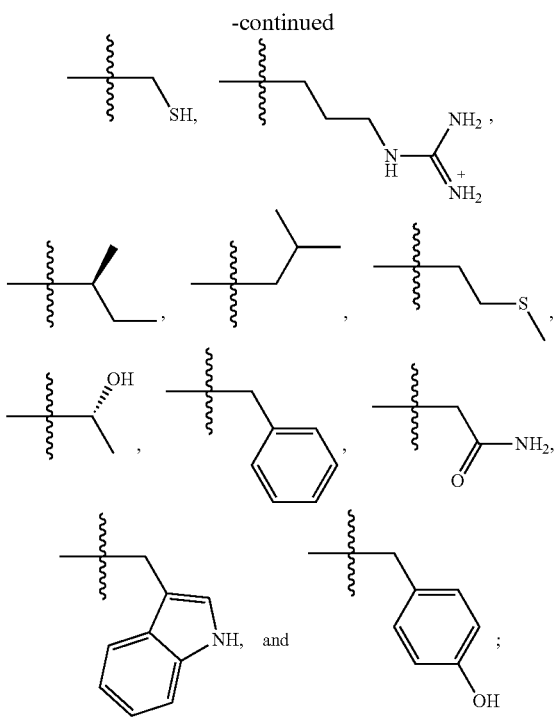

and $R_2$ is selected from the group consisting of saturated and unsaturated $C_5$ to $C_{21}$ linear hydrocarbon chains.

According to some embodiments of the invention, the compound of Formula IB comprises stearoyl alanine, lauroyl alanine or myristyl phenylalanine.

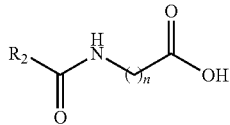

(Formula IC)

where:

$R_2$ is selected from the group consisting of saturated and unsaturated $C_5$ to $C_{21}$ linear hydrocarbon chains; and n=1, 2, 3, 4 or 5.

The compounds of Formulas I, IA, IB and IC, having oil-herding properties, may be used in methods of treating oil-water mixtures. In one embodiment, a method of treating an oil on water mixture to herd the oil and thereby increase the thickness (i.e. depth) of the oil layer comprises contacting the oil-water mixture with a composition having one of the compounds. In another embodiment, a method of preventing or minimizing the spread of an oil on water and thereby maintaining the thickness of the oil phase, comprises applying the herder to the water before it is contacted with the oil. In another embodiment, a method of reducing the adhesion of oil to solid substrates comprises conditioning the solids with a composition having one of the compounds before the solids are contacted with the oil. The conditioning comprises bringing the composition into contact with the solids for a suitable period of time, for example one hour.

Gellants

Replacement of the acid (COOH) group of fatty acid α-amino acid conjugates with other groups capable of acting as hydrogen bond (H-bond) donors and acceptors results in potent phase selective organo gellants. When added to an oil-water mixture, these compounds can increase the viscosity of the oil phase or form a gel. Amides and their derivatives have been demonstrated to provide varying degrees of oil thickening (i.e. viscosity enhancing) and gelling behavior. Among the functional groups which can replace the carboxylic acid group are: primary and secondary amides, hydrazines and hydroxamic acids.

Within the amides and their derivatives of N-fatty acid α-amino acid conjugates, the length of the fatty acid can be varied from C6 to C20 to still provide phase selective organo gellants. Unsaturated bonds within the fatty acid are also tolerated (i.e., alkene and alkynes). The fatty acid component of the N-fatty acid α-amino acid conjugates need not be pure (i.e., a single discrete chemical species). Mixtures of fatty acids can result in a mixture of N-fatty acid α-amino acid conjugates which retain PSOG behavior. Potential sources of fatty acid mixtures include plant and animal oils such as coconut and canola oils and beef tallow.

Formula II is a general formula of amides and their derivatives of N-Fatty acid α-amino acid-based compounds with phase selective gelling activity:

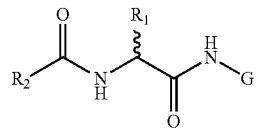

(Formula II)

where:

$R_1$ is selected from the group consisting of:

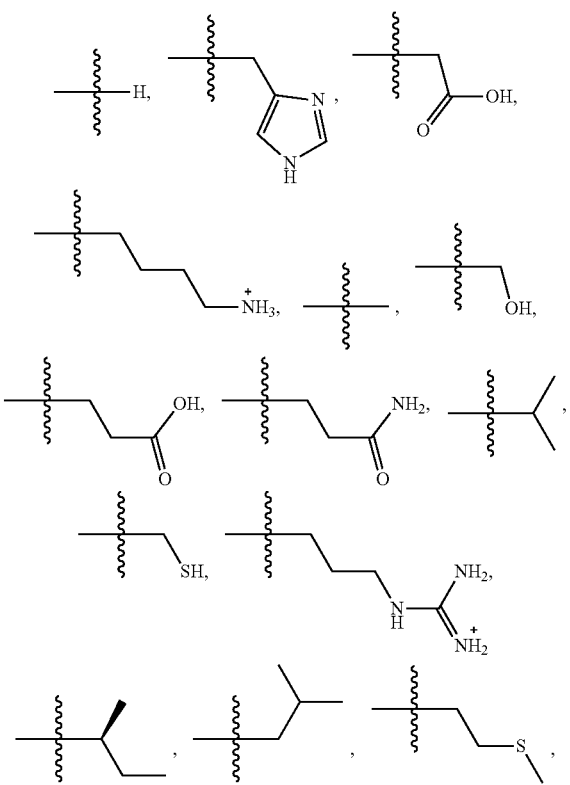

-continued

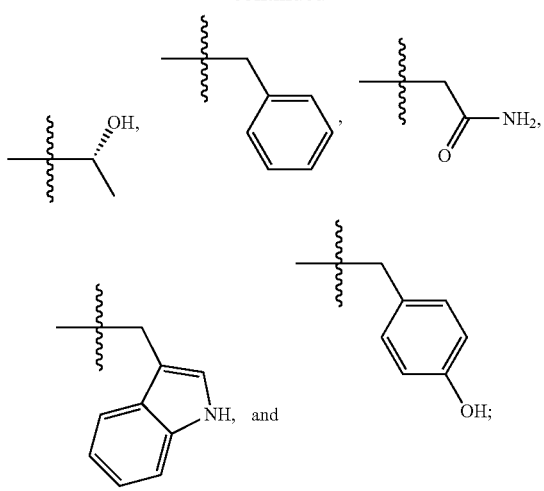

$R_2$ is selected from the group consisting of saturated and unsaturated $C_5$ to $C_{21}$ linear hydrocarbon chains, and

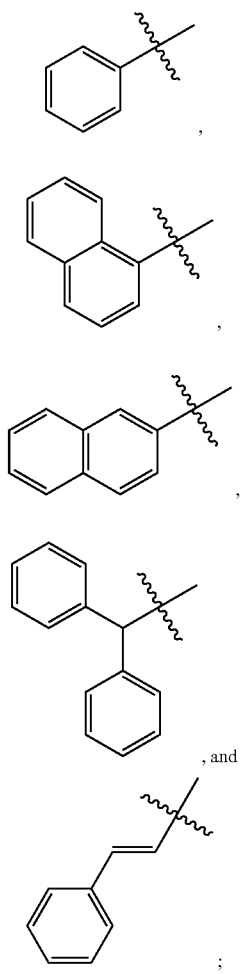

and

G is selected from the group consisting of —H, —$CH_3$, —$NH_2$, —OH, —$OCH_3$, and —$(CH_2)_2OH$.

In some embodiments, the compound of Formula II comprises a compound wherein G is —H. In some embodiments, the compound of Formula II is one of:

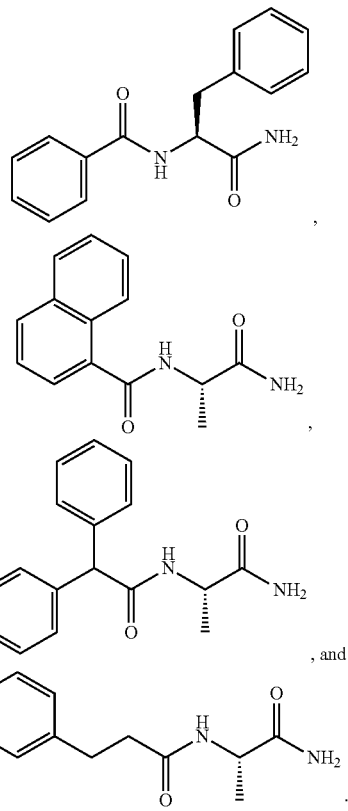

In one embodiment, the compound of Formula II comprises L-Alanine, N-(1-oxododecyl)-, hydrazide.

In addition to chirally pure α-amino acids (using D/L or R/S designation), we have determined that, surprisingly, racemic mixtures could also be employed to prepare PSOGs. The potential to use racemic mixtures as a feedstock provides economic incentives due to the higher costs normally associated with chirally pure materials.

As in the case of parent acid compounds, the analogs presented in Formula II can be administered via different routes. The use of a water-soluble delivery solvent (co-solvent method) to introduce the compounds into a mixture of oil and water is useful for screening for gelling activity. Alternatively, the compound can be delivered as a solid to the oil-water mixture which is then heated to dissolve the compound. Agitation followed by a cooling step results in gel formation. The preferred option is to heat the gellant in a mixture of water and a water-miscible organic solvent until the solid is dissolved. The resulting solution is then cooled to precipitate the gellant. The proportion of organic solvent can vary from 0 to 50% by volume. The most preferred additional option is to heat the PSOG compound in water until it is dissolved. Upon cooling, the PSOG compounds precipitates from solution to form an active suspension of fibrous solids in water. Addition of this suspension to an oil water mixture (or vice versa) followed by agitation results in the formation of a gel.

Figure 3:
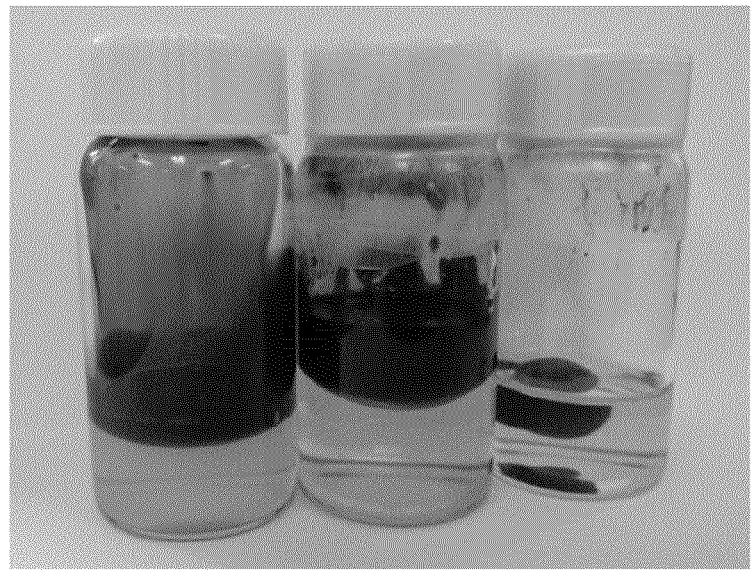
FIG. 3 is a photograph showing the effect of gelling on dilbit-water mixtures.

In some instances, some of the N-fatty acid α-amino acid analogs presented in Formula III, shown below, present as powdery white solids. For some of these compounds an additional option for compound delivery was possible. The compounds could be suspended as a powder in water and the aqueous suspension then added to a mixture of water and oil. Upon agitation, the result was a noticeable thickening of the oil phase and an increase in volume due to the formation of a stable water in oil emulsion. This is illustrated in FIG. 3, showing vials of dilbit (diluted bitumen) and water which, from left to right are a control (untreated), oil treated to a thickened state with a PSOG suspended in water, and oil treated with a PSOG delivered as solution in a water-miscible-solvent to produce a gel pellet. The PSOG used was oleic alaninamide. The ability to deliver phase selective gellants using water as a delivery medium to thicken a hydrophobic phase towards a gel state has not been reported in the literature.

N-fatty acid amino acids and their derivatives which incorporate higher order amino acids such as β and γ analogs also provide potent gellants. These analogs have additional methylene groups in the amino acid group resulting in slightly elongated analogs. Formula III is a general formula of phase selective organo gellants incorporating longer amino acids:

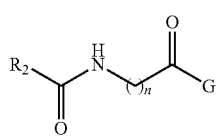

(Formula III)

where:

R$_1$ is selected from the group consisting of saturated and unsaturated C$_5$ to C$_{21}$ linear hydrocarbon chains;

G is selected from the group consisting of —OH, —NH$_2$, —NHNH$_2$, —NOH, NOCH$_3$, and —N(CH$_2$)$_2$OH; and n=2, 3, 4 or 5.

According to one embodiment, the compound of Formula III comprises N-(3-amino-3-oxopropyl) dodecanamide.

Preferred compounds in accordance with Formula III have the general structure of Formula IIIA:

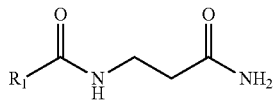

(Formula IIIA)

where R$_1$ is selected from the group consisting of saturated and unsaturated C$_5$ to C$_{21}$ linear hydrocarbon chains.

In some embodiments of Formula IIIA, R$_1$ comprises an even number of carbons, or alternatively, an odd number of carbons.

In some embodiments of Formula IIIA, R$_1$ comprises one of:

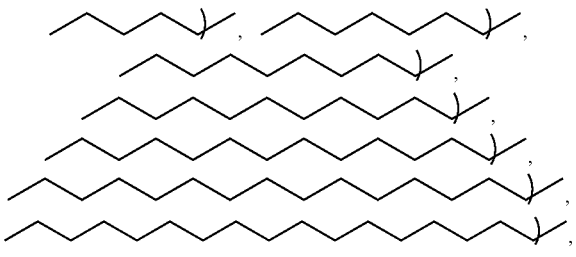

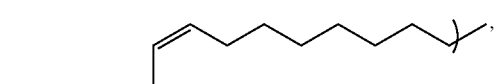

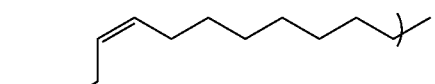

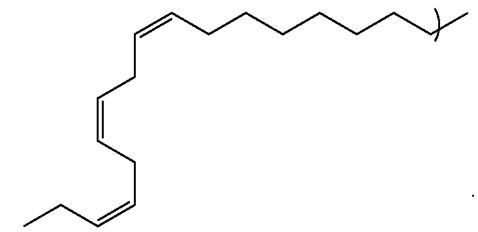

and

The use of β-alanine and longer unsubstituted amino acids and their derivatives removes the stereocenter, which can lower the cost of starting materials.

In some embodiments, the compound of Formula II, III or IIIA comprises one of:

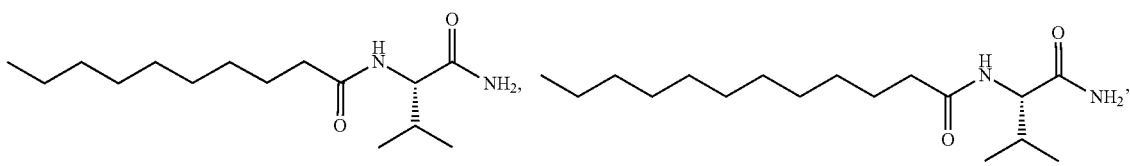

-continued
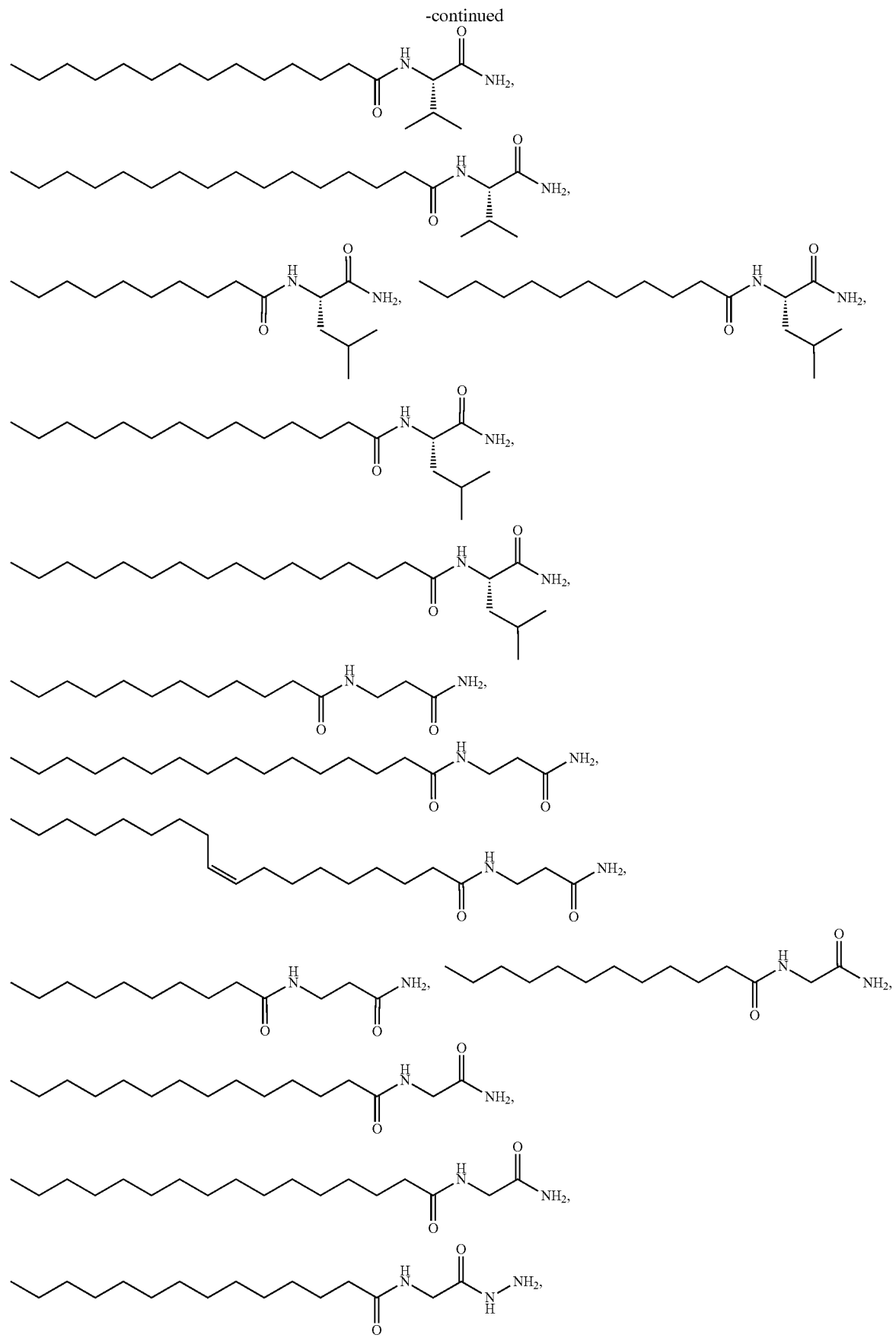

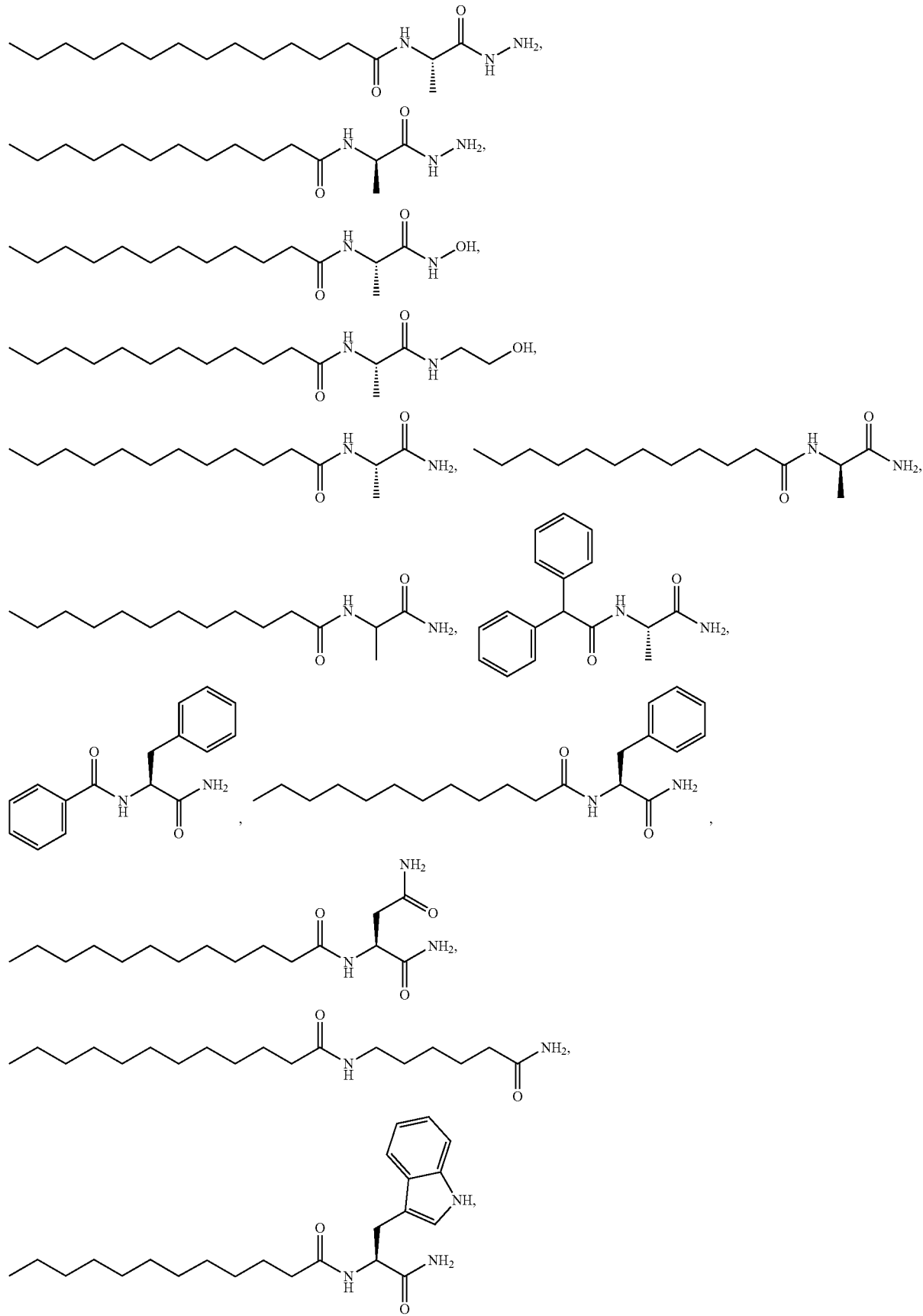

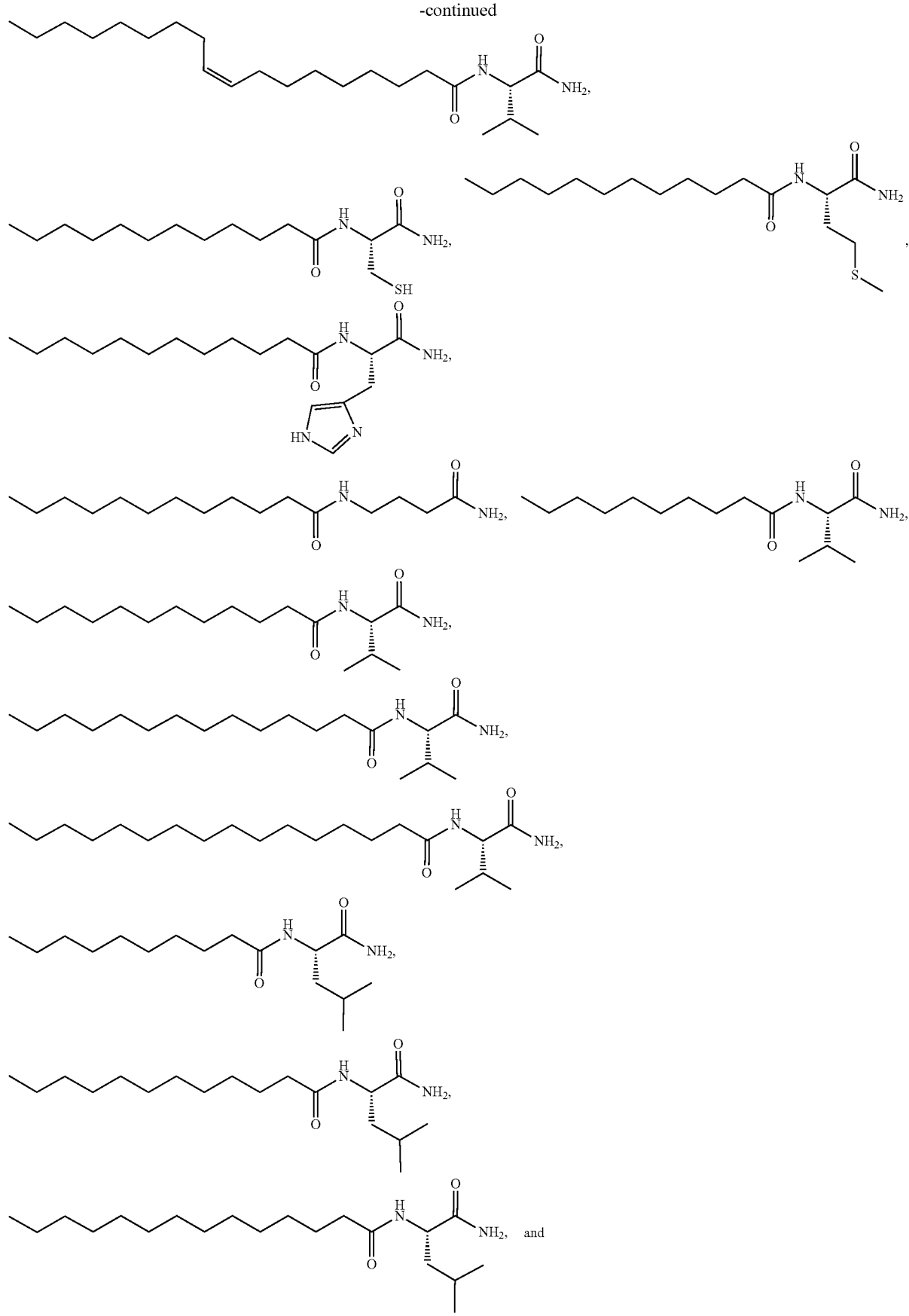

-continued

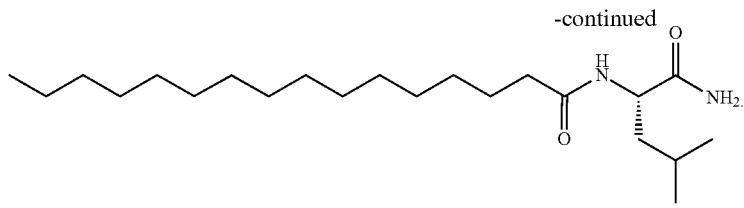

In some embodiments of the invention, one or more compounds in accordance with those disclosed herein, e.g., in accordance with Formulas II, III and IIIA, are part of a composition which has oil-thickening, oil-gelling and/or emulsifying action. The oil thickening, oil gelling and/or emulsification action can be promoted by delivering the compound in a composition with a water-soluble additive that acts as a solubility aid.

Examples of such additives include NaCl, NaBr, urea, glucose, sodium phosphate, polysorbate 20, polysorbate 80, trehalose, sodium tartrate, and citric acid, and mixtures thereof.

As in the case of the α-amino acids and their derivatives, a mixture of fatty acids, such as those derived from plant and animal oils, can be used to make mixtures of compounds with the higher order amino acids and their amide derivatives which retain the ability to selectively gel hydrophobic liquids in the presence of water. Compounds with longer fatty acid groups can also be formulated and delivered as a suspension of a solid in water. Alternatively, the compounds can also be delivered as an active suspension in water. The active suspension in water is formed by heating the solids in water followed by a cooling step to precipitate the compound as fibrous solids.

The oil-water mixture treatment compounds disclosed herein have been determined to be effective at gelling oil, for example in an oil spill situation, when delivered in a carrier that comprises either exclusively water or a low proportion of a water-miscible organic solvent in water. The use of such compositions, by eliminating or reducing the level of organic solvent relative to that suggested in prior art, has the benefit of lessening flammability, thus making the process safer, being less toxic for spill cleanup workers, and having a lower environmental impact. The composition may comprise 0 to 50% by volume organic solvent in the total water-solvent mixture. Suitable organic solvents include ethanol, isopropyl alcohol, 1-butanol, acetonitrile, N,N-dimethylformamide, 1,3-butanediol and 1-propanol.

In one embodiment using a low proportion of organic solvent, the compound is delivered as a solution or suspension in water after being prepared using an organic co-solvent in proportions of 50% by volume or less of solvent to water. The compound, which is a solid, is first treated with a solution comprising a minimal amount of water-miscible organic solvent in water. The compound may either dissolve or suspend in the water-miscible organic solvent, producing a solution or suspension. Heat may be used to dissolve the solid in the solution. The cooled solution or suspension is then added to an oil-water mixture to effect gelation of the oil phase.

In an alternative embodiment using a low proportion of organic solvent, water is added to a mixture of the compound in an organic solvent to precipitate the compound and bring the proportion of organic solvent to 50% by volume or less in the carrier solution. The resulting suspension, which is composed predominantly of water, is then added to an oil-water mixture to effect gelation of the oil phase.

In a further alternative embodiment using a low proportion of organic solvent, the compound is removed from a water-organic solvent mixture. The solvent mixture may comprise 0 to 50% by volume organic solvent in the total water-solvent mixture. The compound is present in the solvent as wetted solids. The removal of the wetted solids may be done by a variety of mechanical means, including the use of a filter or by centrifugation of the mixture. The removed wetted solids are then added to an oil-water mixture to effect gelation of the oil phase.

In a further alternative embodiment using only water, the compound is heated and dissolved in water. The solution is allowed to cool to precipitate the compound as low density solids. Addition of this active suspension to a mixture of oil and water followed by gentle mixing results in absorption of the oil and gel formation.

In a further embodiment, a supramolecular gellant that is an amphiphile capable of self-assembly is added to water and heated until dissolved. Upon cooling, the compound reforms as solids via a self-assembly. The re-formed solids have higher surface area and higher void fraction than pre-dissolved material due to the self-assembly process, which may produce structures which include, but are not limited to, sheets, fibers, ribbons and spherulites. The re-formed solids are hydrophobic/oleophilic. The void spaces are originally occupied by water. Upon contact with an oil phase, the water is displaced by the oil. The volume of the gellant is reduced as the oil is absorbed. The final volume of the gelled oil is approximately equal to the original volume of the oil. Examples of gellants capable of forming structures via self-assembly which can gel oils include N-(3-amino-3-oxopropyl) dodecanamide, (S)—N-(1-hydrazineyl-1-oxopropan-2-yl) dodecanamide, 3-(Oleoylamino) propionamide and 1-[(S)-2-Amino-3-methylbutyrylamino]-1-dodecanone.

The compounds disclosed herein offer distinct advantages over what has been reported in the patent and academic literature. The herders disclosed herein represent improvement over currently-available options in many ways which include: (a) elimination of the use of synthetic polymer based chemistries; (b) reduction or elimination of the use of organic carrier solvents in favour of aqueous-based delivery; (c) the use of bio-based feedstocks and, (d) herding agents which are biodegradable.

The thickeners (viscosity enhancers) and gellants disclosed herein represent an advance in the field for a variety of reasons which include one or more of: (a) the elimination of the need to use heat to dissolve the gellant in a hydrophobic phase-water mixture to effect gelation; (b) the elimination of the need to use high proportions of a water-miscible organic delivery solvent; (c) improvement in loading requirements from 10-20% w/v to less than 2.5% w/v; (d) the elimination of the need to use an organic wetting solvent; (e) improved gelling times to less than 20 minutes;

(e) the use of bio-based feedstocks to produce agents which are of lower environmental toxicity; and (f) the reduction of costs for potential feedstock by the elimination of starting materials that contain a chiral center; (g) the ability to use heat to dissolve and re-suspend the gellant in an all water solvent system which eliminates the need to use an organic solvent; and (h) biodegradability.

EXAMPLES

Example 1

Synthesis of
N-(3-amino-3-oxopropyl)dodecanamide

B-alaninamide (3 g, 24.1 mmol) was added to chloroform (80 mL). This mixture was cooled in an ice bath. Triethylamine (5.36 g, 53 mmol) was added via syringe. The mixture was stirred for two minutes after which lauroyl chloride (5.80 g, 26.5 mmol) was added dropwise via syringe. The reaction was allowed to warm to room temperature and stirred overnight. The product was isolated by suction filtration as a white powdery solid (5.86 g, 90%).

Example 2

Synthesis of L-Alanine, N-(1-oxododecyl)-, hydrazide

L-alanine methyl ester hydrochloride (4 g, 28.6 mmol) was dissolved in chloroform (60 mL). Triethylamine (6.38 g, 63 mmol) was added via syringe. The mixture was cooled in an ice. Lauroyl chloride (6.9 g, 31.5 mmol) was added dropwise via syringe. The ice bath was removed and the reaction was stirred at room temperature overnight. The crude reaction was diluted with chloroform (300 mL). The organic phase was washed with 0.2 M HCl (1.5 L), 5% NaHCO$_3$ (800 mL) and saturated brine (300 mL). The organic phase was dried over sodium sulphate and filtered. The solvent was removed under reduced pressure to yield the methyl ester as a white solid in quantitative yield.

The methyl ester (1.5 g, 5.1 mmol) was dissolved in methanol (40 mL). Hydrazine monohydrate (7.70 g, 154 mmol) was added dropwise. The reaction was stirred overnight at room temperature. Additional methanol (50 mL) was added to the reaction which was stirred for an additional four hours. The methanol was removed under reduced pressure. The crude was taken up in chloroform (400 mL). The organic phase was washed with brine (75 mL). The chloroform was separated and the remaining water and rag layer were washed with ethyl acetate (400 mL). The combined organic phases were dried over sodium sulphate and the solvent removed under reduced pressure to yield the product as a white solid in quantitative yield.

Example 3

Preparation of L-Alanine, N-(1-oxododecyl)-, sodium salt

L-Alanine, N-(1-oxododecyl)- (1 g, 3.7 mmol) was suspended in water (50 mL). Sodium hydroxide (0.15 g, 3.7 mmol) was added as a solid. The mixture was agitated. Additional water was added if necessary to solubilize the salt. The solution was used as is.

Example 4

Gelling or Thickening Method for
PSOGs—Co-Solvent Method

PSOGs were screened against dilbit, diesel and sunflower. The dilbit used in the Examples herein was prepared by dissolving bitumen in naphtha in a 65:35 ratio of bitumen to naphtha. A typical screening method utilized a 1:4 ratio of hydrophobic liquid to water (i.e., 1 mL oil product to 4 mL water) in a 20 mL vial. The gellant (22.5 mg) was dissolved in a carrier solvent, which was typically methanol, ethanol or isopropanol. Heat was applied to dissolve the solid if necessary. The gellant solution was transferred to the oil-water mixture and the vial was capped. Agitation was applied and the mixture allowed to settle. Gel formation typically presented as the formation of an oil pellet or a thickening of the oil phase.

Example 5

Gelling or Thickening Method for PSOGs—Dry
Solid Delivery with Heating

Using a mixture of 1 mL of oil to 4 mL water in a 20 mL vial, 22.5 mg of gellant (oleic-β-alanine amide) was added as a solid and the vial capped. Heat was applied until the solid dissolved. The oil-water mixture was allowed to cool to room temperature undisturbed. Gel formation typically presented as a gel cap over the water layer or as a thickened (higher viscosity) oil.

Example 6

Gelling or Thickening Method for
PSOGs—Delivery as an Aqueous Suspension

Gellants which presented as fine powdery solids were suspended in water (4-5 mL). The suspension was sonicated to reduce the particle size if necessary. The suspension was added to a mixture of 1 mL oil to 4 mL water in a 20 mL vial. The vial was capped and the mixture agitated. Thickening of the oil, likely due to the formation of an emulsion, could be observed within 15 minutes.

Example 7

Measurement of Herding Capacity as Measured by
Slick Thickness

The herder formulation was pre-dosed into 1 L of water in a flat glass pan under which was a 1×1 cm grid. A known volume of oil was applied to the pre-dosed water. A digital photo of the oil slick was recorded. The image was processed using ImageJ in order to calculate the area of the slick. Since volume and area are known, it is possible to calculate the thickness of the slick as a function of herder dosing. Compounds that maximize the thickness of the slick are considered better oil-herders.

Figure 9:
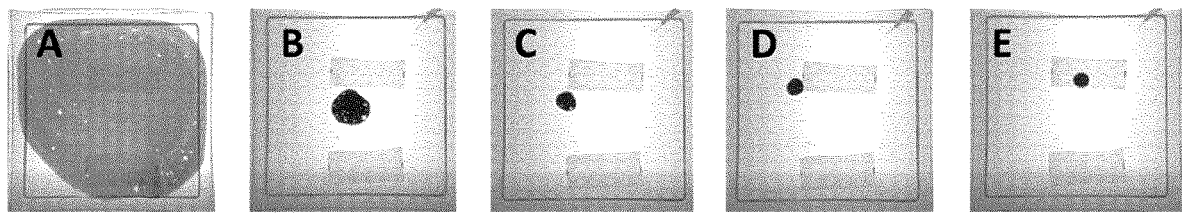
FIG. 9 is a series of photographs showing herding of dilbit (i.e., slick retraction) using an aqueous solution of L-phenylalanine, N-(1-oxotetradecyl)-, sodium salt. (Example 7)

Alternatively, an oil was applied to water in a pan and allowed to spread. A herder (e.g. L-phenylalanine, N-(1-oxotetradecyl)-, sodium salt) was applied to the water to retract the slick (i.e. decrease surface area while increasing the thickness/depth of the oil layer). Overhead photography was used to capture the herding process. The images were processed to determine the area of the slick and allow for calculation of the slick thickness (FIG. 9).

Example 8

Evaluation of Gelling Ability—Solution Phase Delivery

Figure 4:
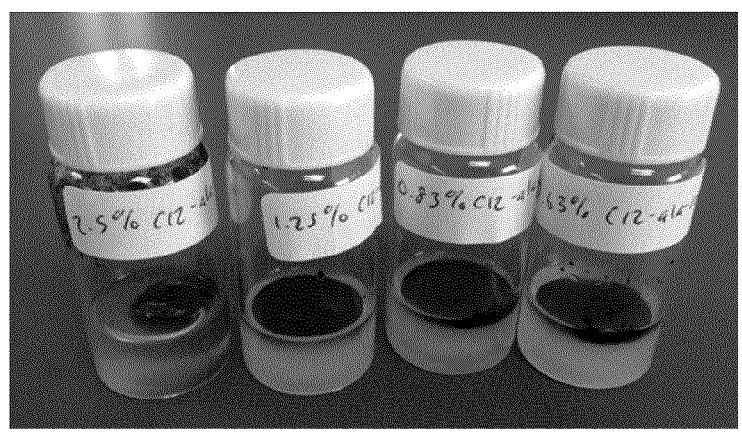
FIG. 4 is a photograph showing gel formation evaluation with dodecanoyl-L-alanine via solvent delivery at 2.5, 1.25, 0.83 and 0.63% w/v (Example 8).

Four portions of the prior art compound dodecanoyl-L-alanine of differing masses were weighed out and each dissolved in 1 mL of isopropyl alcohol. These four solutions were added to four separate 20 mL vials of 1:4 mL dilbit and water. The amounts of dodecanoyl-L-alanine used in the different portions resulted in dosing ratios of 2.5, 1.25, 0.83 and 0.63% w/v relative to dilbit. The vials were agitated and the results are shown in FIG. 4. Gel formation was evaluated qualitatively. It was found that the dodecanoyl-L-alanine only formed a gel at a dosing of 2.5% w/v.

Figure 5:
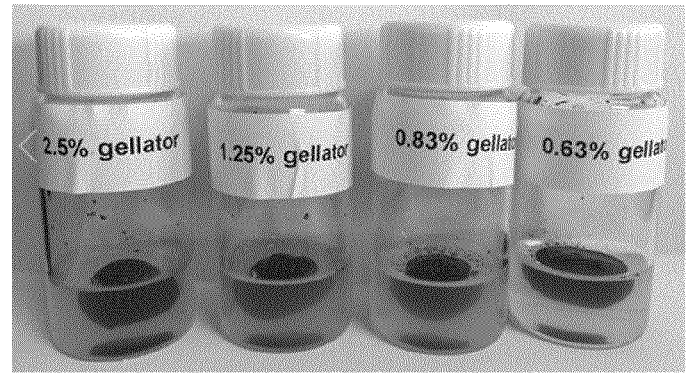
FIG. 5 is a photograph showing gel formation evaluation with dodecanoyl-β-alaninamide via solvent delivery at 2.5, 1.25, 0.83 and 0.63% w/v (Example 8).

This procedure was repeated with dodecanoyl-β-alaninamide. Four portions of dodecanoyl-β-alaninamide of differing masses were weighed out and each dissolved in 1 mL of isopropyl alcohol. These four solutions were added to four separate 20 mL vials containing 1 mL dilbit and 4 mL water. The amounts of dodecanoyl-β-alanine used in the different portions resulted in dosing ratios of 2.5, 1.25, 0.83 and 0.63% w/v relative to dilbit. The vials were agitated and the results are shown in FIG. 5. Gel formation was evaluated qualitatively. It was found that the dodecanoyl-β-alaninamide formed a gel at all dosing ratios evaluated from 2.5 to 0.63% w/v.

Example 9

Aqueous Suspension Delivery of Gellants

Figure 6:
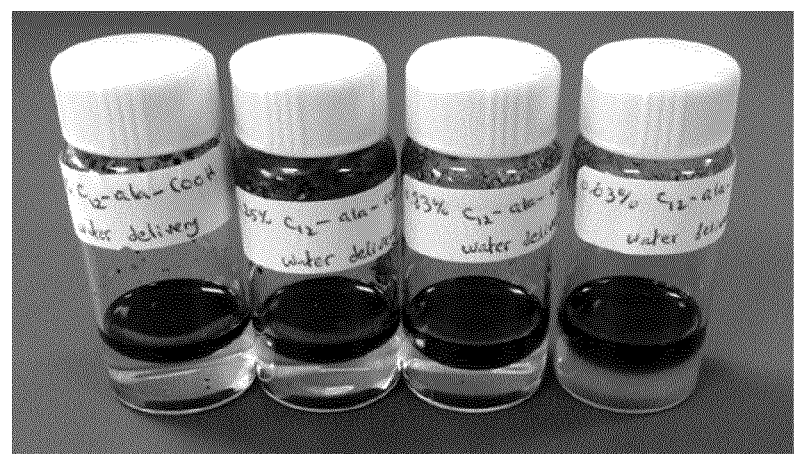
FIG. 6 is a photograph showing oil thickening evaluation with dodecanoyl-L-alanine via suspended solids delivery at 2.5, 1.25, 0.83 and 0.63% w/v. (Example 9)

Four portions of prior art compound dodecanoyl-L-alanine of differing masses were weighed out and each suspended in 1 mL of water. These four suspensions were added to four separate 20 mL vials of 1:4 mL dilbit and water. The amounts of dodecanoyl-L-alanine used in the different portions resulted in dosing ratios of 2.5, 1.25, 0.83 and 0.63% w/v relative to dilbit. The vials were agitated and the results are shown in FIG. 6. Oil thickening was evaluated qualitatively. It was found that the dodecanoyl-L-alanine did not thicken the oil at any of the dosing levels tested when applied as a solid suspended in water.

Figure 7:
FIG. 7 is a photograph showing oil thickening evaluation with dodecanoyl-β-alaninamide via suspended solids delivery at 2.5, 1.25, 0.83 and 0.63% w/v. (Example 9)

This experiment was repeated with dodecanoyl-β-alaninamide. Four portions of dodecanoyl-β-alaninamide of differing masses were weighed out and each suspended in 7 mL of water. These four suspensions were added to four separate 20 mL vials of 1:4 mL dilbit and water. The amounts of dodecanoyl-β-alaninamide used in the different portions resulted in dosing ratios of 2.5, 1.25, 0.83 and 0.63% w/v relative to dilbit. The vials were agitated and the results are shown in FIG. 7. Oil thickening was evaluated qualitatively. It was found that the dodecanoyl-3-alaninamide thickened the oil at all dosing levels which were evaluated from 2.5 to 0.63% w/v.

Example 10

Assessment of Herder Activity

Stearoyl alanine was dissolved in isopropyl alcohol. An aliquot of this solution was added to 1 L of water in a pan. The final dosage of stearoyl alanine was 0.77 mg in 1 L of water. Dilbit (2.27 g) was added. An overhead digital photo was taken of the oil after 10 minutes. The photo was analyzed to determine the area of the oil which could be used to calculate the thickness of the oil layer. The oil slick was determined to be 2.9 mm thick.

Silsurf, (trademark) a commercial herder added to 1 L of water in a glass pan for a final dosing of 1 mg. Dilbit (1.61 g) was added to the water. An overhead digital photo was taken of the oil after 10 minutes. The photo was analyzed to determine the area of the oil which could be used to calculate the thickness of the oil layer. The oil slick was determined to be 2.0 mm thick. The stearoyl alanine herder produced a thicker oil layer than Silsurf at a comparable dosage.

Example 11

Demonstration of Gelling Activity Using Mixed Organic Solvent-Water

The gellant oleic-p-alaninamide (25 mg) was suspended in 5 mL of a mixed solvent system composed of 2:3 1,4-butanediol and water. The mixture was heated to dissolve the solids. Upon cooling, the gellant precipitates as a cotton-like mass. Addition of this suspension to a mixture 1:4 oil (i.e. dilbit, diesel, or crude oil) and seawater followed by gentle agitation resulted in gelling of the oil phase in less than 1 minute.

Example 12

Demonstration of Gelling Activity without the Need for an Organic Solvent

Figure 8:
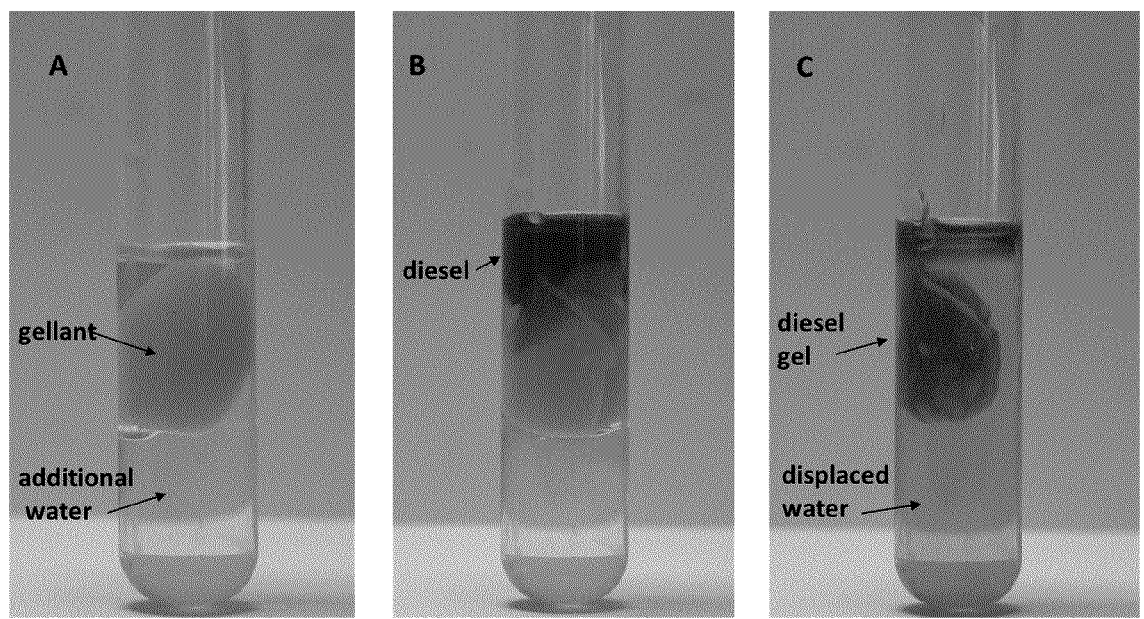
FIG. 8 is a series of photographs showing gelling of dyed diesel without the use of an organic solvent at 2 wt. % (Example 11).

The gellant oleic-β-alaninamide (25 mg) was suspended 5 mL of water which was dyed pink for visualization purposes. The mixture was heated to dissolve the gellant. Upon cooling, the gellant precipitated as a cotton-like mass which retains the water. Addition of dye free water demonstrated that there is very little to no leaching of the dyed water from the gellant mass (FIG. 8A). Upon the addition of diesel, which has been dyed blue, the hydrophobic phase entered the gellant mass upon contact and displaced the dyed water (FIGS. 8B and 8C) to produce the gelled diesel.

Example 13

Measuring Biodegradability of Select Herder and Gellant

Figure 10:
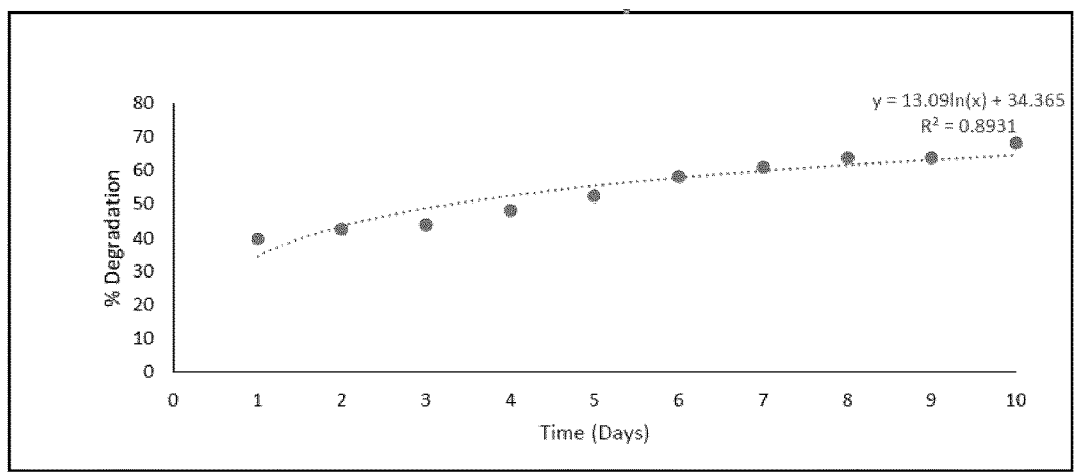
FIG. 10 is the plot of % degradation for determination of the biodegradability of the herder L-phenylalanine, N-(1-oxotetradecyl)-, sodium salt. (Example 13)
Figure 11:
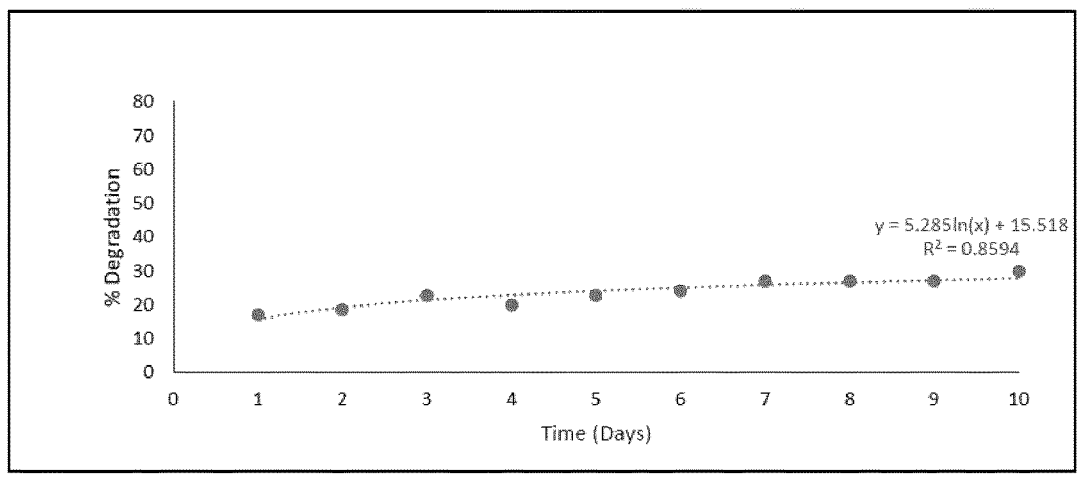
FIG. 11 is the plot of % degradation for determination of the biodegradability of the gellant oleic-β-alaninamide. (Example 13)

The herder L-phenylalanine, N-(1-oxotetradecyl)-, sodium salt and the gellant oleic-β-alaninamide were assessed for biodegradability in using OECD 301F guideline, manometric respirometer test. The herder reduced the theoretical oxygen demand by 68% in the 10-day window and is considered readily biodegradable. The gellant reduced the theoretical oxygen demand by 30% in the 10-day window and is classified as inherently biodegradable. The plot of data for % degradation for the herder and gellant is shown in FIGS. 10 and 11 respectively.

Example 14

Reduction of Oil Adhesion by Conditioning with Aqueous Herder Solution

Glass bead were used as a model substrate. The beads were weighed and transferred into a pre-weighed 60 mL plastic syringe. The beads were immersed in an aqueous solution of herder, C14-L-Phe-COONa, for 1 hour. An oil layer of conventional crude oil was added to the surface of the herder solution above the glass beads. The oil was lowered hydrostatically to immerse the beads in oil for 1 hour after which the oil was raised hydrostatically above the level of the beads. The water above the oil and beads were both removed. The mass of the oil retained on the glass beads was calculated as the difference between the mass of the oil-coated beads and the initial mass of the beads. The results are shown in Table 1.

TABLE 1

Effect of herder on oil adhesion on glass beads

| Herder concentration (g/L) | Average mass of conventional crude retained (g) |
|---|---|
| 10 | 1.8 |
| 2.9 | 1.6 |
| 0.57 | 1.3 |
| 0.086 | 1.9 |
| Control (no herder) | 3.2 |

The ability of a herder solution to decrease the amount of oil adhesion on the model substrates is evident. The amount of oil adhering to the glass beads can be decreased by as much as 50% by pre-conditioning the beads with an aqueous solution of herder.

The invention claimed is:

1. A composition for treating a mixture of oil and water to herd the oil, comprising a water-miscible organic solvent and one or more compounds of Formula IB:

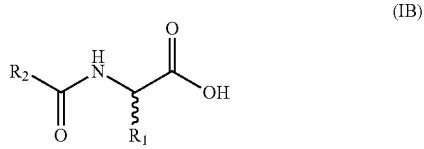

(IB)

where:

$R_1$ is selected from the group consisting of:

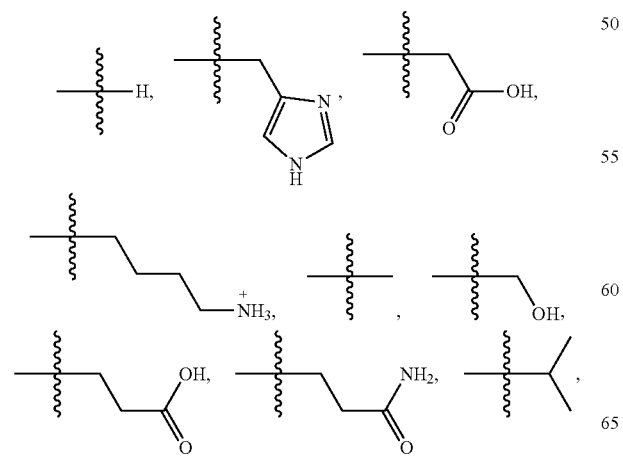

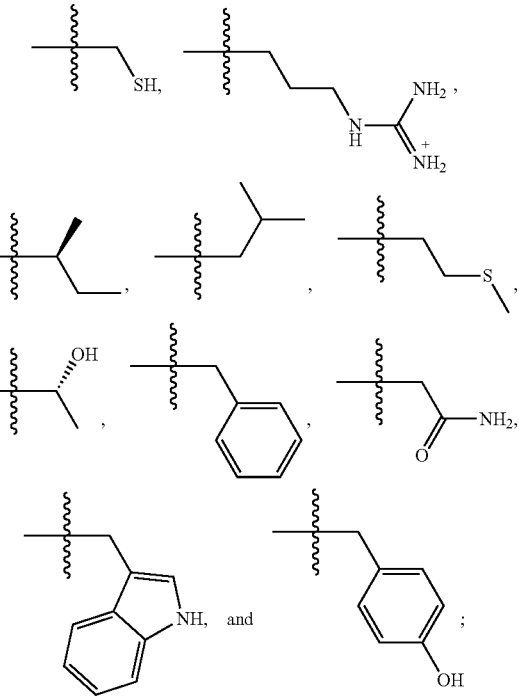

and $R_2$ is selected from the group consisting of saturated and unsaturated $C_5$ to $C_{21}$ linear hydrocarbon chains.

2. A composition according to claim 1, wherein the compound is stearoyl alanine.

3. A composition according to claim 1, wherein the compound is lauroyl alanine.

4. A composition according to claim 1, wherein the compound is myristoyl phenylalanine.

5. A composition for treating a mixture of oil and water to herd the oil on the surface of the water, comprising L-Alanine, N-(1-oxododecyl)-, sodium salt or its enantiomer or the racemic mixture, L-Phenylalanine, N-(1-oxododecyl)-, sodium salt or its enantiomer or the racemic mixture, L-Phenylalanine, N-(1-oxotetradecyl)-, sodium salt or its enantiomer or the racemic mixture, or L-tyrosine, N-(1-oxohexadecyl)-, sodium salt or its enantiomer or the racemic mixture.

6. A composition according to claim 1, further comprising a water-soluble delivery solvent.

7. A composition for treating a mixture of oil and water to gel or increase the viscosity of the oil on the surface of the water, comprising one of:

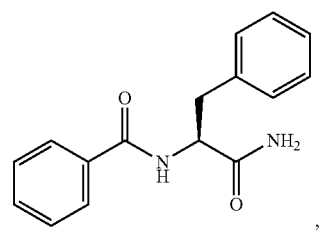

-continued

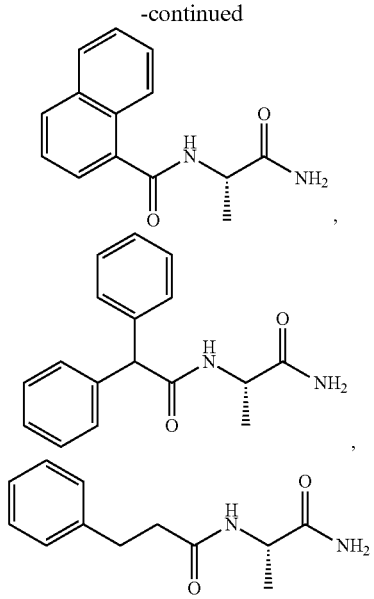

and (S)—N-(1-aminol-1-oxopropan-2-yl)dodecanamide.

8. A composition for treating a mixture of oil and water to thicken or gel the oil on the surface of the water, comprising a compound of Formula III:

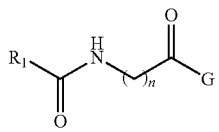
(III)

where:
R$_1$ is selected from the group consisting of saturated and unsaturated C$_5$ to C$_{21}$ linear hydrocarbon chains;
G is selected from the group consisting of —OH, —NH$_2$, —NHNH$_2$, —NOH, —NOCH$_3$, and —N(CH$_2$)$_2$OH; and
n is =2.

9. A composition for treating a mixture of oil and water to thicken or gel the oil on the surface of the water, comprising N-(3-amino-3-oxopropyl) dodecanamide.

10. A compound for treating a mixture of oil and water to thicken or gel the oil on the surface of the water, comprising a compound of Formula IIIA:

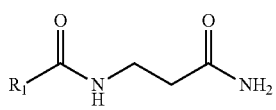
(IIIA)

where R$_1$ is selected from the group consisting of saturated and unsaturated C$_5$ to C$_{21}$ linear hydrocarbon chains, and wherein R$_1$ comprises (i) an even number of carbons, (ii) an odd number of carbons, or (iii) one of:

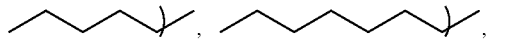

and

11. A composition for treating a mixture of oil and water to thicken or gel the oil on the surface of the water, comprising a compound that is one of:

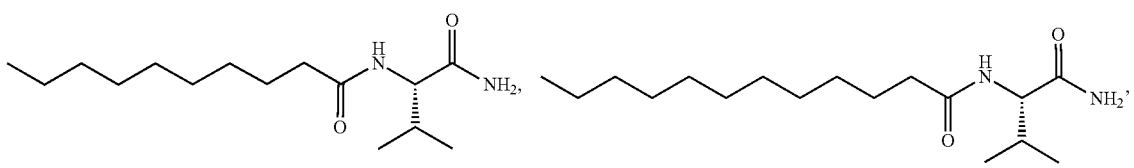

-continued
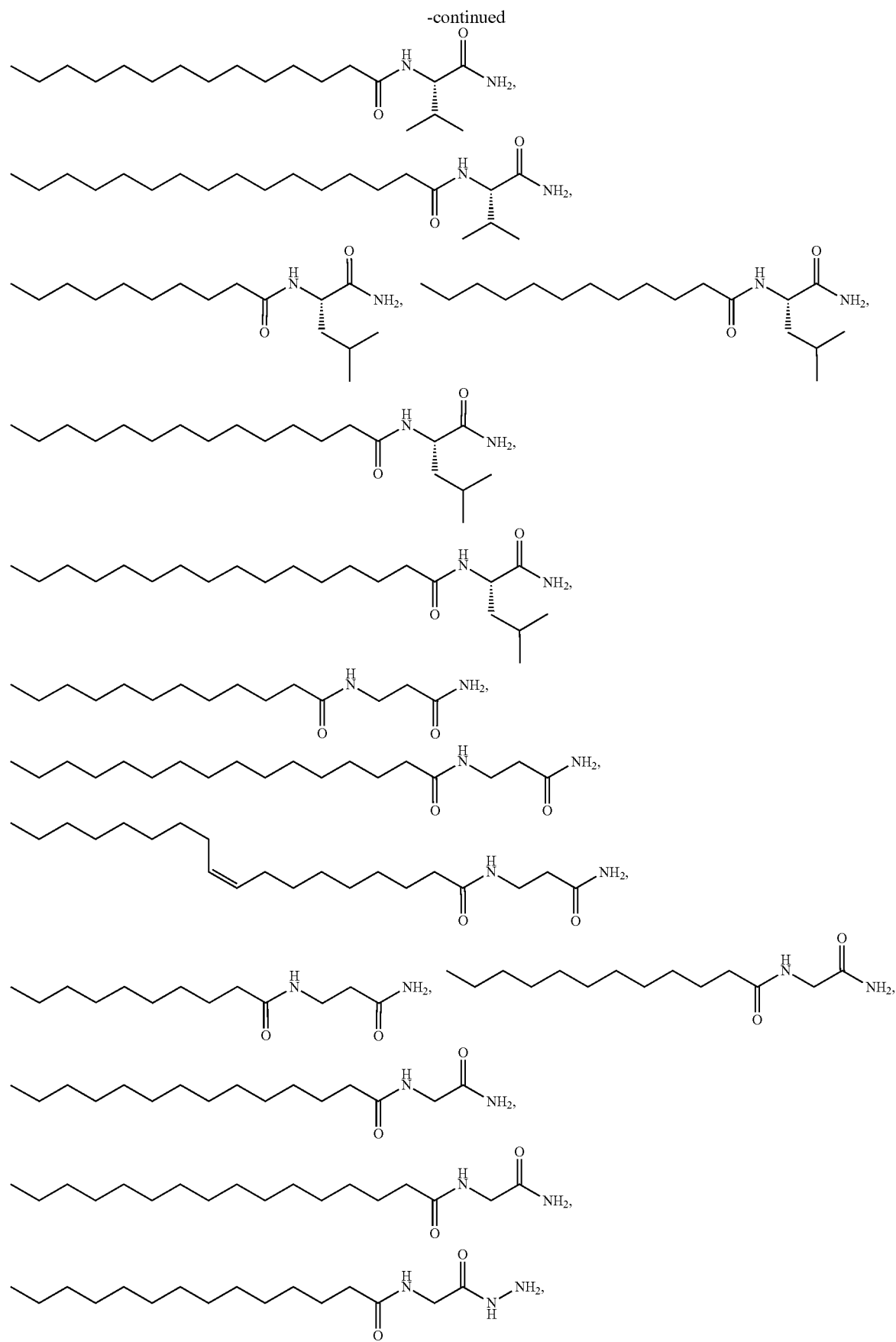

-continued
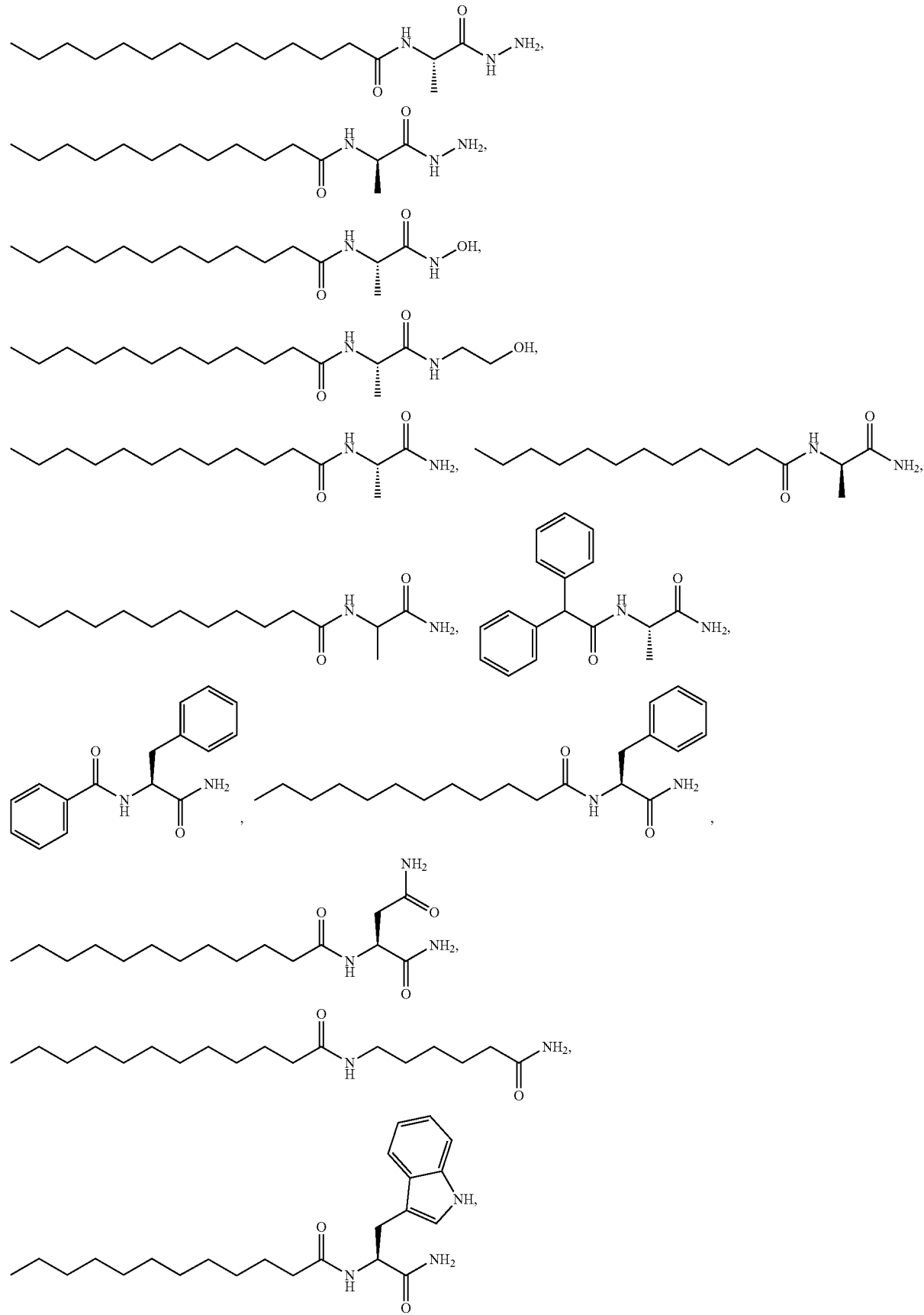

-continued
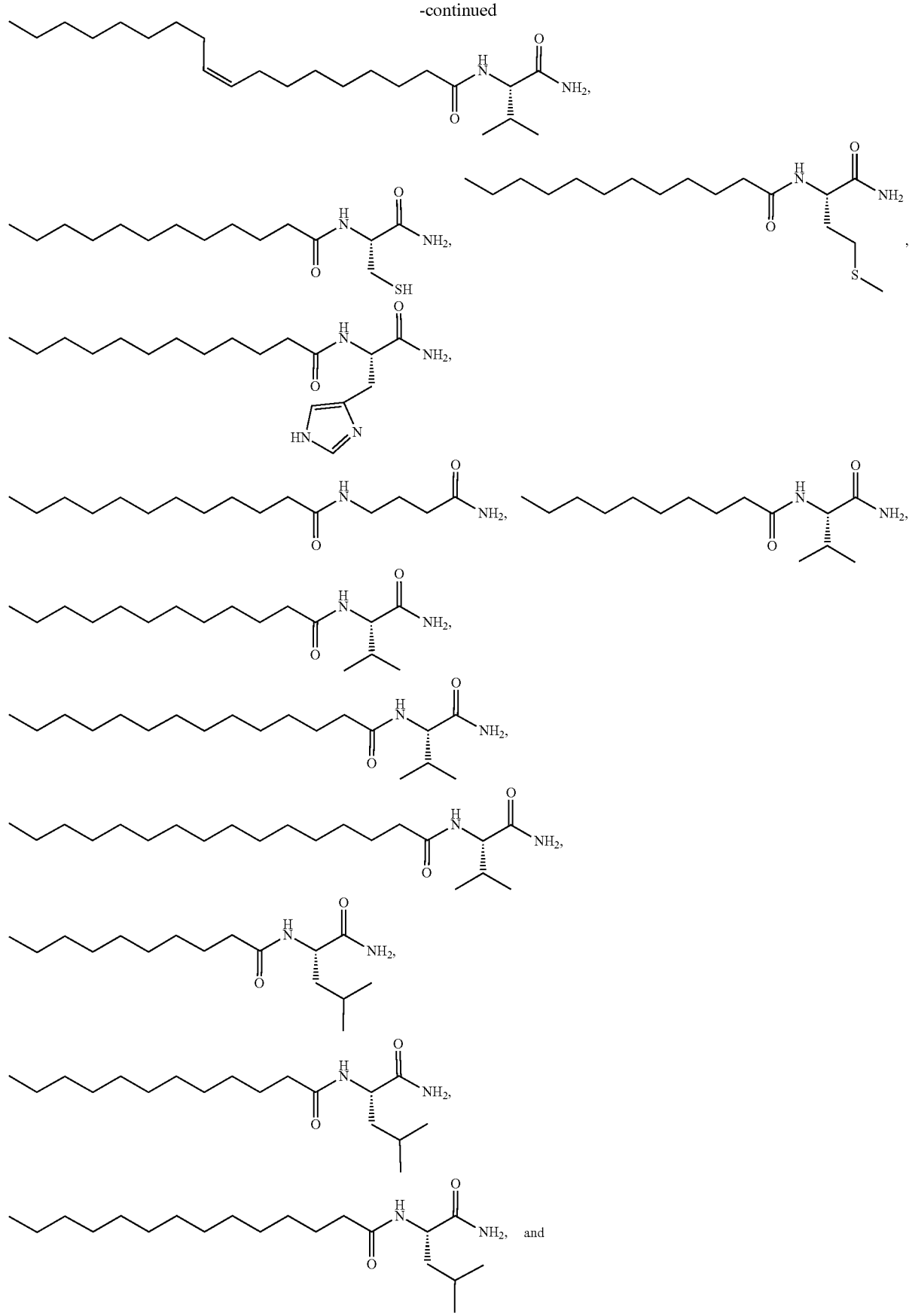

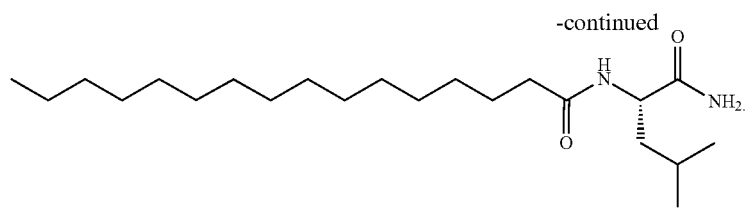

12. A composition comprising a mixture of two or more compounds as defined in claim 11.

13. A method of treating an oil-water mixture to gel or increase the viscosity of the oil, the method comprising the steps of:

(a) preparing a solution or suspension comprising (i) one or more compounds in accordance with Formula II:

(II)

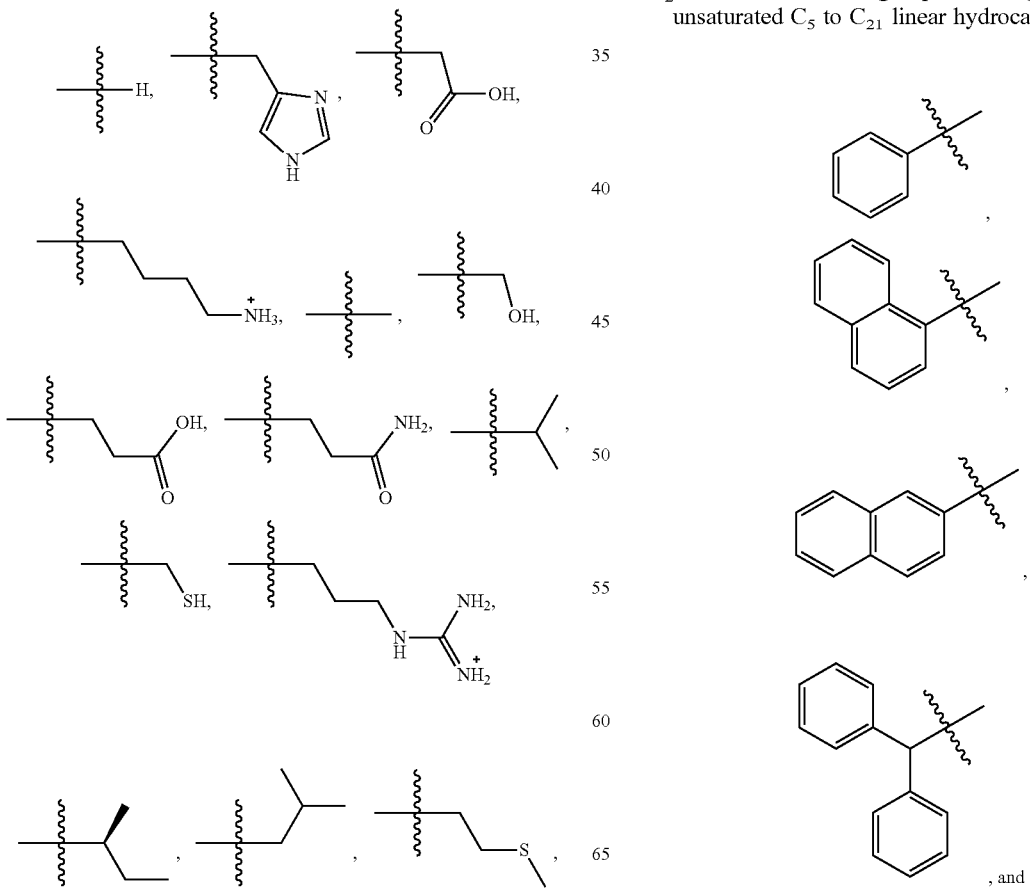

where:

$R_1$ is selected from the group consisting of:

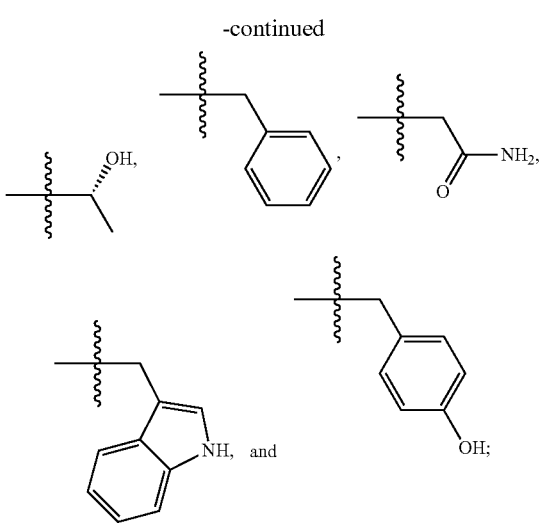

$R_2$ is selected from the group consisting of saturated and unsaturated $C_5$ to $C_{21}$ linear hydrocarbon chains, and -continued

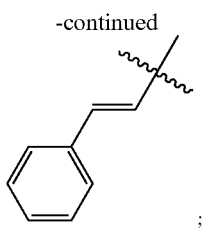

and
G is selected from the group consisting of —H, —CH$_3$, —NH$_2$, —OH, —OCH$_3$, and —(CH$_2$)$_2$OH and (ii) a carrier solution comprising a water-miscible organic solvent and water, in which the organic solvent comprises in the range 0 to 50% by volume of said carrier solution; and
(b) contacting the oil with the solution or suspension prepared in step (a).

14. A method of treating an oil-water mixture to gel or increase the viscosity of the oil, the method comprising the steps of:
(a) preparing a suspension comprising one or more compounds in accordance with Formula III

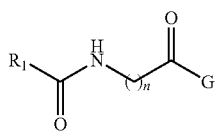

where:
R$_1$ is selected from the group consisting of saturated and unsaturated C$_5$ to C$_{21}$ linear hydrocarbon chains;
G is selected from the group consisting of —OH, —NH$_2$, —NHNH$_2$, —NOH, —NOCH$_3$, and —N(CH$_2$)$_2$OH; and
n is 2, 3, 4 or 5, wherein the suspension is prepared by (i) adding the compounds or compositions to water, (ii) applying heat to dissolve the solids, and (iii) cooling the solution to precipitate the solids; and
(b) contacting the oil with the suspension.

15. A method according to claim 14, wherein the oil comprises one of dilbit, diesel and conventional crude oil.

16. A method according to claim 15, wherein the amount of the compound used is in the range of 0.63 to 2.5% w/v.

17. A method according to claim 14 wherein the water comprises sea water.

18. A method of treating an oil-water mixture comprising the steps of:
(a) suspending a supramolecular gellant in water to form a suspension;
(b) heating the suspension until the gellant is dissolved;
(c) cooling the suspension to form a hydrophobic structure or structures with a high surface area and high void volume; and
(d) contacting the hydrophobic structure or structures with an oil-water mixture and thereby gelling the oil.

19. A method according to claim 18, wherein the gellant is selected from the group consisting of N-(3-amino-3-oxopropyl) dodecanamide, (S)—N-(1-hydrazineyl-1-oxopropan-2-yl)dodecanamide, 3-(Oleoylamino)propionamide and 1-[(S)-2-Amino-3-methylbutyrylamino]-1-dodecanone.

20. A method of treating a mixture of oil and water to herd the oil on the surface of the water comprising the steps of:
(a) preparing a solution comprising one or more compounds and a carrier,
(b) contacting the oil with the solution,
wherein the one or more compounds are one of the Formula I:

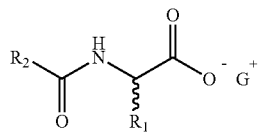

where:
R$_1$ is selected from the group consisting of:

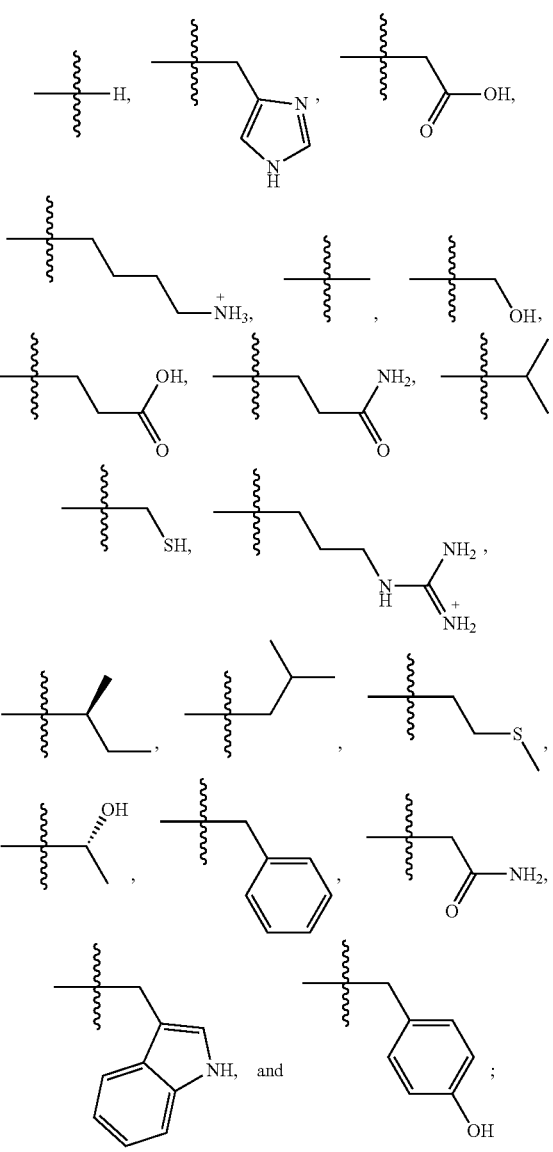

R$_2$ is selected from the group consisting of saturated and unsaturated C$_5$ to C$_{21}$ linear hydrocarbon chains; and
G is a cation.

21. The method according to claim 20, wherein the cation is selected from the group consisting of Na, K, Li, piperidinium, piperazinium, imidazolium, N-methyl imidazolium, and benzimidazolium.

22. A method of treating a mixture of oil and water to herd the oil on the surface of the water comprising the steps of:
(a) preparing a solution comprising one or more compounds and a carrier, and
(b) contacting the oil with the solution, wherein the one or more compounds are one of the Formula IC:

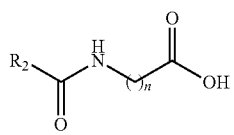
(IC)

where:
$R_2$ is selected from the group consisting of saturated and unsaturated $C_5$ to $C_{21}$ linear hydrocarbon chains; and
n is 1, 2, 3, 4 or 5.

23. A method of treating a mixture of oil and water to thicken or gel the oil on the surface of the water comprising the steps of:
(a) preparing a solution comprising one or more compounds and a carrier, and
(b) contacting the oil with the solution,
wherein the one or more compounds are one of the Formula II:

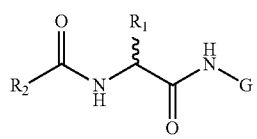
(II)

where:
$R_1$ is selected from the group consisting of:

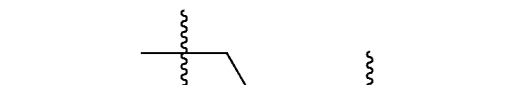
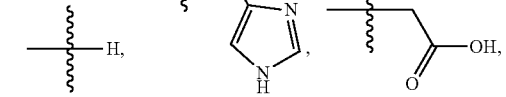
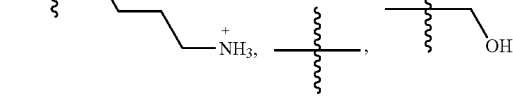
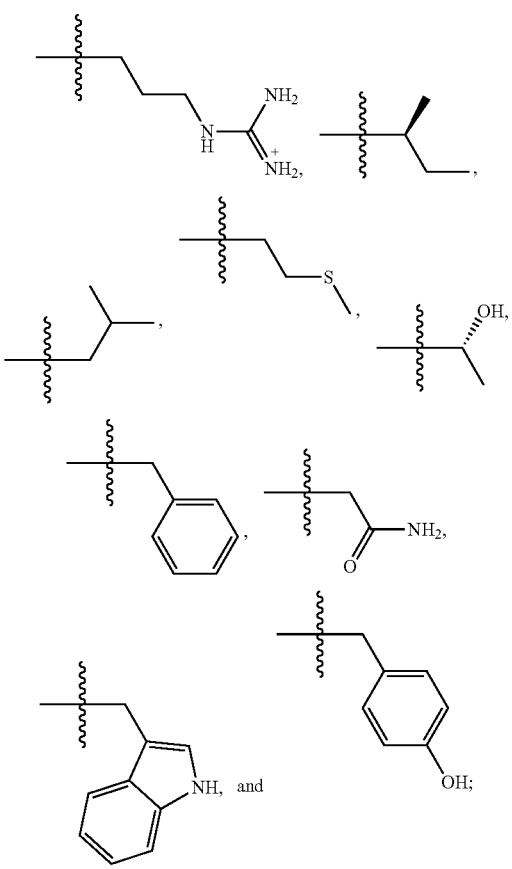

$R_2$ is selected from the group consisting of saturated and unsaturated $C_5$ to $C_{21}$ linear hydrocarbon chains, and

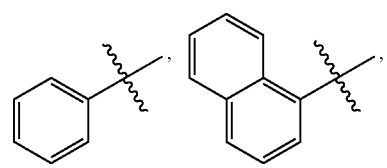
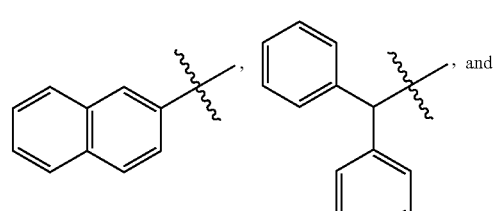
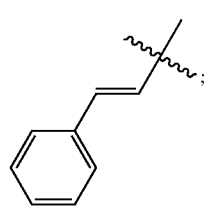

and
G is selected from the group consisting of —H, —CH₃, —NH₂, —OH, —OCH₃, and —(CH₂)₂OH.

24. A method according to claim 23, wherein G is —H.

25. A method of treating a mixture of oil and water to thicken or gel the oil on the surface of the water comprising the steps of:
(a) preparing a solution comprising one or more compounds and a carrier, and
(b) contacting the oil with the solution,
wherein the one or more compounds are one of the Formula III:

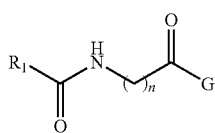
(III)

where:
R₁ is selected from the group consisting of saturated and unsaturated C₅ to C₂₁ linear hydrocarbon chains;
and
G is selected from the group consisting of —OH, —NH₂, —NHNH₂, —NOH, —NOCH₃, and —N(CH₂)₂OH;
and
n is 2, 3, 4 or 5.

26. A method of treating a mixture of oil and water to thicken or gel the oil on the surface of the water comprising the steps of:
(a) preparing a solution comprising one or more compounds and a carrier, and
(b) contacting the oil with the solution,
wherein the one or more compounds are one of the Formula IIIA:

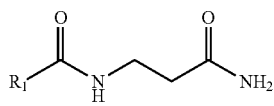
(IIIA)

where R₁ is selected from the group consisting of saturated and unsaturated C₅ to C₂₁ linear hydrocarbon chains.

* * * * *